(12) United States Patent
Leonardi et al.

(10) Patent No.: US 7,071,197 B2
(45) Date of Patent: Jul. 4, 2006

(54) N,N-DISUBSTITUTED DIAZOCYCLOALKANES

(75) Inventors: Amedeo Leonardi, Milan (IT); Gianni Motta, Barlassima (IT); Carlo Riva, Varese (IT); Rodolfo Testa, Vignate (IT)

(73) Assignee: Recordati S.A., Chiasso (CH)

( * ) Notice: Subject to any disclaimer, the term of this patent is extended or adjusted under 35 U.S.C. 154(b) by 0 days.

(21) Appl. No.: 10/463,222

(22) Filed: Jun. 16, 2003

(65) Prior Publication Data

US 2004/0072822 A1 Apr. 15, 2004

Related U.S. Application Data

(60) Provisional application No. 60/509,038, filed on Jun. 14, 2002.

(30) Foreign Application Priority Data

Jun. 14, 2002 (IT) .......................... MI2002A1328

(51) Int. Cl.
*A61K 31/495* (2006.01)
*C07D 295/092* (2006.01)
(52) U.S. Cl. ................. 514/255.03; 544/394; 540/575; 514/218
(58) Field of Classification Search ................ 544/394; 514/255.03
See application file for complete search history.

(56) References Cited

U.S. PATENT DOCUMENTS

| | | | |
|---|---|---|---|
| 4,122,176 A | 10/1978 | Katsube et al. | |
| 4,217,349 A | 8/1980 | Katsube et al. | |
| 5,340,812 A | 8/1994 | Cliffe | |
| 5,346,896 A | 9/1994 | Ward et al. | |
| 5,462,934 A | 10/1995 | Goto et al. | |
| 5,627,177 A | 5/1997 | Cliffe et al. | |
| 5,693,642 A | 12/1997 | Cliffe et al. | |
| 5,798,362 A | 8/1998 | Leonardi et al. | |
| 6,239,135 B1 | 5/2001 | Kohlman et al. | |
| 6,306,861 B1 | 10/2001 | Leonardi et al. | |
| 6,365,591 B1 | 10/2001 | Leonardi et al. | |
| 6,358,958 B1 | 3/2002 | Kohlman et al. | |
| 6,403,594 B1 | 6/2002 | Leonardi et al. | |
| 6,514,976 B1 | 2/2003 | Kohlman et al. | |
| 2001/0003749 A1 | 6/2001 | Godfrey et al. | |

FOREIGN PATENT DOCUMENTS

| | | |
|---|---|---|
| BE | 642084 | 7/1964 |
| EP | 0 605 230 | 7/1994 |
| EP | 0 924 205 | 6/1999 |
| FR | 2 527 605 | 12/1983 |
| WO | WO 92/06082 | 4/1992 |
| WO | WO 94/15919 | 7/1994 |
| WO | WO 99/06382 | 2/1999 |
| WO | WO 99/06383 | 2/1999 |
| WO | WO 99/31077 | 6/1999 |
| WO | 03/106443 A1 * | 12/2003 |

OTHER PUBLICATIONS

Testa et al. BJU International, vol. 87, p. 256-264 (Feb. 2001).*
Vippagunta et al. Advanced Drug Delivery Reviews, vol. 48, p. 3-26 (2001).*
Olivier et al. Medline Abstract for Prog. Drug Res. vol. 52, p. 103-165 (1999).*
Abdel-Magid, A. et al., (1996) Reductive Amination of Aldehydes and Ketones with Sodium Triacetoxyborohydride. Studies on Direct and Indirect Reductive Amination Procedures, *J. Org. Chem.*, 61:3849-3862.
Andersson K-E, (1988) Current Concepts in the Treatment of Disorders of Micturition, *Practical Therapeutics*, 35:477-494.
Bliss C.I., (1938) The Determination of the Dosage-Mortality Curve from Small Numbers, *Quart. J. Pharm.*, 11:192-216.
Brougham et al., (1987) Oxidation Reactions Using Magnesium Monoperphthalate: A Comparison with m-Chloroperoxybenzoic Acid, *Synthesis*, 1015-1017.
Cheng et al., (1973) Relationship Between the Inhibition Constant ($K_1$) and the Concentration of Inhibitor which causes 50 percent Inhibition ($I_{50}$) of an Enzymatic Reaction, *Biochemical Pharmacology*, 22:3099-3108.

(Continued)

*Primary Examiner*—Emily Bernhardt
(74) *Attorney, Agent, or Firm*—Darby & Darby

(57) ABSTRACT

N,N-Disubstituted diazocycloalkanes of the formula I

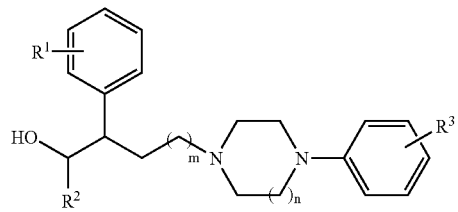

($R^1$=halogen, $R^2$=($C_3$–$C_8$)-cycloalkyl, $R^3$=($C_1$–$C_4$)-alkoxy or ($C_1$–$C_4$)-haloalkoxy group, m is 1 or 2 and n is 1 or 2, have affinity for serotonergic receptors. These compounds and their enantiomers, diastereoisomers, N-oxides, polymorphs, solvates and pharmaceutically acceptable salts are useful in the treatment of patients with neuromuscular dysfunction of the lower urinary tract and diseases related to 5-$HT_{1A}$ receptor.

4 Claims, 2 Drawing Sheets

OTHER PUBLICATIONS

De Groat, (1990) Central neural control of the lower urinary tract, *Neurobiol. Of Incontinence, Ciba Found. Symp.*, 151:27-56.

De Lean A. et al., (1978) Simultaneous analysis of families of sigmoidal curves: application to bioassay, radioligand assay, and physiological dose-response curves, *Am. J. Physiol.*, 235:E97-E102.

Dray A., (1985) The Rat Urinary Bladder, A Novel Preparation for the Investigation of Central Opioid Activity In Vivo, *J. of Pharm. Methods*, 13:157-165.

Fargin A. et al., (1988) The genomic clone G-21 which resembles a beta-adrenergic receptor sequence encodes the 5-HT1A receptor, *Nature*, 335:358-360.

Felluga et al., (1989) "Carbo- and Heterocyclization Reactions of 2-(4-Morpholinyl)-1-Phenylpropene and Nitroolefins", *Tetrahedron*, 45:5667-5678.

Goodman & Gilman, (1996) The Pharmacological Basis of Therapeutics 9th Ed., McGraw-Hill p. 11-17.

Guarneri L. et a., (1993) Effects of Drugs Used in the Therapy of Detrusor Hyperactivity on the Volume-Induced Contraction of the Rat Urinary Bladder, *Pharmacological Research*, 27:173-187.

Guarneri L. et al., (1991) Effects of Different Drugs on the Cystometrogram in Conscious Rats, *Pharmacological Research*, 24:175-187.

Guarneri L. et al., (1994) A Review of Flavoxate: Pharmacology and Mechanism of Action, *Drugs of Today*, 30:91-98.

Lepor et al., (1993) "Medical Therapy for Benign Prostatic Hyperplasia", *Urology*, 42:483-501.

Maggi C.A. et al., (1984) Evidence for the Involvement of Arachidonic Acid Metabolites in Spontaneous and Drug-induced Contractions of Rat Urinary Bladder, *J. of Pharm. And Experimental Therapeutics*, 230:500-513.

Maggi C.A. et al., (1986) Somatovesical and Vesicovesical Excitatory Reflexes in Urethane-Anaesthetized Rats, *Brain Research*, 380:83-93.

March J., (1977) Oxidation or Dehydrogenation of Alcohols to Aldehydes and Ketones, *Advanced Organic Chemistry II Ed.*, McGraw-Hill, 1082-1084.

March J., (1977) Ozonolysis; Oxidative Cleavage of Double Bonds, *Advanced Organic Chemistry II Ed.*, McGraw-Hill, 1090-1096.

March J., (1977) The Addition of Organometallic Compounds to Aldehydes and Ketones, *Advanced Organic Chemistry II Ed.*, McGraw-Hill, 836-841.

Marx M. et al., (1984) Reactivity-Selectivity in the Swern Oxidation of Alcohols Using Dimethyl Sulfoxide-Oxalyl Chloride, *J. Org. Chem.*, 49:788-793.

McGuire E., (1986) Neuromuscular Dysfunction of the Lower Urinary Tract, *Campbell's Urology*, 1:616-638.

Nagata et al., (1970) "Hydrocyanation. Part IX. Synthesis of β-Cyano-aldehydes by Conjugate Hydrocyanation of Allylideneamines Followed by Hydrolysis", *J. Chem. Soc. (C)*, pp. 2355-2364.

Nahm S. et al., (1981) N-methoxy-N-methylamides as Effective Acylating Agents, *Tetrahedron Letters*, 22:3815-3818.

Nilvebrant L., (2001) Clinical experiences with tolterodine, *Life Sciences*, 68:2549-2556.

Ruffmann R., (1988) A Review of Flavoxate Hydrochloride in the Treatment of Urge Incontinence, *J. of International Medical Research*, 16:317-330.

Tricklebank M.D. et al., (1985) Subtypes of the 5-HT Receptor Mediating the Behavioural Responses to 5-Methoxy-N, N-dimethyltryptamine in the Rat, *European J. of Pharmacology*, 117:15-24.

Crossfire Beilstein online database Jun. 29, 1989 Beilstein Institut zur Forderung der Chemischen Wissenschaften, Frankfurt am Main, DE; Database accession No. 2087440.

Crossfire Beilstein online database Aug. 28, 1992 Beilstein Institut zur Forderung der Chemischen Wissenschaften, Frankfurt am Main, DE; Database accession No. 5019111.

Forbes et al., (1980) "Applications of Substituted Arylacetaldehydes in the Total Synthesis of seco-Mesembrane Alkaloids. Part 1. The Total Synthesis of (‡-O-Methyljoubertiamine", *J.C.S. Perkins I*, p. 906-910.

Vasileva et al., (1991) "Synthesis and biological activity of α-phenyl-β-(1-alkylaryl-4-piperazinyl)propiophenones", *Dokl. Bulg. Akad. Nauk.*, 44:55-58.

Natova et al., (1978) "Structure of some Mannich bases", *God. Vissh. Khim.-Tekhnol. Isnt., Sofia*, 24:37-46.

\* cited by examiner

N,N-DISUBSTITUTED DIAZOCYCLOALKANES

CROSS REFERENCE TO RELATED APPLICATIONS

The present application claims the benefit of priority under 35 U.S.C. § 119(e) of provisional application No. 60/509,038, filed Jun. 14, 2002, and the benefit of priority under 35 U.S.C. § 119(a)–(d) of Italian patent application MI2002A 001328, filed Jun. 14, 2002. Each of the foregoing applications is hereby incorporated herein by reference in its entirety.

FIELD OF THE INVENTION

The invention relates to novel N,N-disubstituted diazocycloalkanes having affinity for serotonergic receptors, to pharmaceutical compositions thereof and to uses for such compounds and compositions.

BACKGROUND OF THE INVENTION

In mammals, micturition (urination) is a complex process that requires the integrated action of the bladder, its internal and external sphincters, the musculature of the pelvic floor and neurological control over these muscles at three levels (in the bladder wall or sphincter itself, in the autonomic centres of the spinal cord and in the central nervous system at the level of the pontine micturition centre (PMC) in the brainstem (pons) under the control of the cerebral cortex) (De Groat, *Neurobiology of incontinence*, Ciba Foundation Symposium 151:27, 1990). Micturition results from contraction of the detrusor muscle, which consists of interlacing smooth-muscle fibres, under the control of the parasympathetic autonomic system originating from the sacral spinal cord. A simple voiding reflex is triggered by sensory nerves for pain, temperature and distension that run from the bladder to the sacral spinal cord. However, sensory tracts from the bladder reach the PMC too, generating nerve impulses that normally suppress the sacral spinal suppression of cortical inhibition of the reflex arc, and relaxing the muscles of the pelvic floor and external sphincter. Finally, the detrusor muscle contracts and voiding occurs. Abnormalities of lower-urinary tract function, e.g., dysuria, incontinence and enuresis, are common in the general population. Dysuria includes urinary frequency, nocturia and urgency, and may be caused by cystitis (including interstitial cystitis), prostatitis or benign prostatic hyperplasia (BPH) (which affects about 70% of elderly males), or by neurological disorders. Incontinence syndromes include stress incontinence, urgency incontinence, overflow incontinence and mixed incontinence. Enuresis refers to the involuntary passage of urine at night or during sleep.

Previously, treatment of neuromuscular dysfunction of the lower urinary tract involved administration of compounds that act directly on the bladder muscles, such as flavoxate, a spasmolytic drug (Ruffman, *J. Int. Med. Res.* 16:317, 1988) which is also active on the PMC (Guarneri et al., *Drugs of Today*, 30:91, 1994), or anticholinergic compounds such as oxybutynin (Andersson, *Drugs* 36:477, 1988) and tolterodine (Nilvebrant, *Life Sci.* 68(22–23): 2549, 2001). The use of α1-adrenergic receptor antagonists for the treatment of BPH is common too, but is based on a different mechanism of action (Lepor, *Urology*, 42:483, 1993). However, treatments that involve direct inhibition of the pelvic musculature (including the detrusor muscle) may have unwanted side effects, such as incomplete voiding or accommodation paralysis, tachycardia and dry mouth (Andersson, *Drugs* 35:477, 1988). Thus, it would be preferable to utilize compounds that act via the central nervous system to, for example, affect the sacral spinal reflex and/or the PMC inhibition pathways in a manner that restores normal functioning of the micturition mechanism.

U.S. Pat. No. 5,346,896 discloses 5-HT$_{1A}$ binding agents which may be used in the treatment of CNS disorders, such as, for example, anxiety.

U.S. Pat. Nos. 6,239,135; 6,358,958 and 6,514,976 disclose aryl piperazine compounds that bind to 5-HT$_{1A}$ receptors.

SUMMARY OF THE INVENTION

The invention provides 5-HT$_{1A}$ receptor antagonists, compositions thereof, and methods of using such antagonists.

Accordingly, in certain embodiments the invention provides compounds having the general formula I

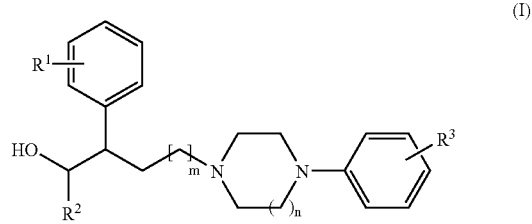

(I)

wherein:
$R^1$ represents a halogen atom,
$R^2$ represents a $(C_3-C_8)$-cycloalkyl group,
$R^3$ represents a $(C_1-C_4)$-alkoxy or $(C_1-C_4)$-haloalkoxy group,
m is 1 or 2, and
n is 1 or 2,
or an enantiomer, optical isomer, diastereomer, N-oxide, crystalline form, hydrate, solvate or pharmaceutically acceptable salt thereof.

In certain embodiments, a compound of formula I is 1-[4-cyclohexyl-4-hydroxy-3-(2-fluorophenyl)-butyl]-4-(2-methoxyphenyl)-piperazine.

In other embodiments, a compound of formula I is 1-[4-cyclohexyl-4-hydroxy-3-(2-fluorophenyl)-butyl]-4-[2-(2,2,2-trifluoroethoxy)-phenyl]-piperazine.

In certain embodiments, the invention provides isomers of the aforementioned compounds of formula I, as, for example, a pure enantiomer or, alternatively, a mixture of any two or more enantiomers in any proportion. Preferably, enantiomers of compounds of formula I are provided in predetermined amounts.

The invention also includes metabolites of the foregoing compounds of formula I having the same type of activity, hereinafter referred to as active metabolites.

The invention also includes prodrugs which are metabolized in the body to generate any of the foregoing compounds.

In certain embodiments, the invention also provides pharmaceutical compositions comprising a compound of formula I, or an enantiomer, optical isomer, diastereomer, N-oxide, crystalline form, hydrate, solvate or pharmaceutically acceptable salt thereof, in admixture with a pharmaceutically acceptable diluent or carrier.

In other embodiments, the invention provides a method for treating or preventing disorders of the urinary tract in a mammal (preferably a human) in need thereof, comprising administering an effective amount of a compound of formula I, or an enantiomer, optical isomer, diastereomer, N-oxide, crystalline form, hydrate, solvate or pharmaceutically acceptable salt thereof, to prevent or ameliorate at least one condition selected from among the group consiting of urinary urgency, overactive bladder, increased urinary frequency, decreased urinary compliance (decreased bladder storage capacity), cystitis (including interstitial cystitis), incontinence, urine leakage, enuresis, dysuria, urinary hesitancy and difficulty in emptying the bladder.

In other embodiments the invention provides methods for reducing the frequency of bladder contractions due to bladder distension in a mammal (such as a human) in need thereof by administering an effective amount of at least one compound of the present invention to reduce the frequency of bladder contractions due to bladder distension to the mammal.

In other embodiments the invention provide methods for increasing urinary bladder capacity in a mammal (such as a human) in need thereof by administering an effective amount of at least one compound of the present invention to increase urinary bladder capacity to the mammal.

In yet another embodiment, the present invention provides a method for treating a mammal suffering from a central nervous system (CNS) disorder manifest in a serotonergic dysfunction by administering an effective amount of at least one compound of the present invention to treat the CNS disorder. Such dysfunctions include, but are not limited to, anxiety, depression, hypertension, sleep/wake cycle disorder, feeding disorders, behaviour disorders, sexual dysfunction and cognition disorders in mammals (particularly in humans) associated with stroke, injury, dementia, and originated by neurological development, attention-deficit hyperactivity disorders (ADHD), drug addiction, drug withdrawal, irritable-bowel syndrome. Treatment may be effected by delivering a compound of the invention to the environment of a 5-HT$_{1A}$ serotonergic receptor, for example, to the extracellular medium (or by systemically or locally administering the compound to a mammal possessing such a 5-HT$_{1A}$ receptor) an amount of a compound of the invention effective in the treatment of the aforementioned disorders.

In a preferred embodiment, the invention provides methods for treating a mammal (including a human) suffering from a urinary tract disorder by administering at least one compound of the invention to the environment of a 5HT$_{1A}$ receptor in an amount effective to increase the duration of bladder quiescence with no contractions. More highly preferred are compounds and/or amounts administered which accomplish an increase in the duration of bladder quiescence is with little or no effect (e.g., decrease or increase) on micturition pressure.

For treating the above disorders, the compounds of the invention may be administered in combination with other agents such as, for example, antimuscarinic drugs, α1-adrenergic antagonists, inhibitors of the cyclooxygenase enzyme, which may inhibit both COX1 and COX2 isozymes or which may, alternatively, be selective for COX2 isozyme, and NO donor derivatives thereof.

DETAILED DESCRIPTION OF THE INVENTION

Figure 1:
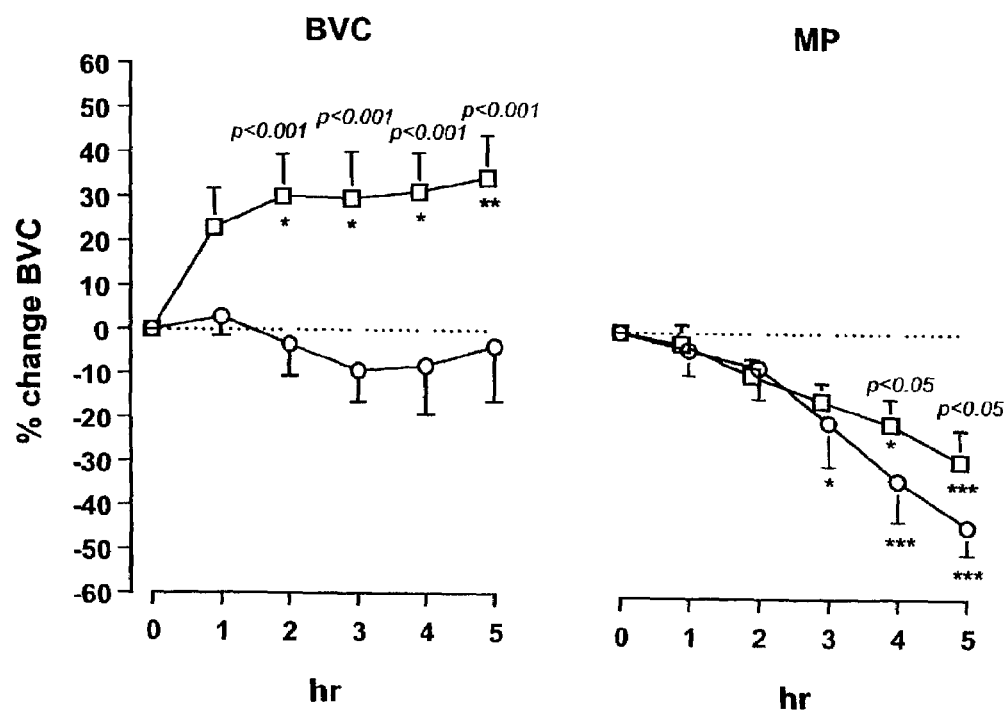
FIG. 1 shows the change versus time of bladder volume capacity (BVC) and micturition pressure (MP) in rats after oral administration of vehicle (circles) or 10.0 mg/kg of the compound 1-[4-cyclohexyl-4-hydroxy-3-(2-fluorophenyl)-butyl]-4-(2-methoxyphenyl)-piperazine (upper TLC Rf) (squares).

The invention provides compounds represented by a general formula I:

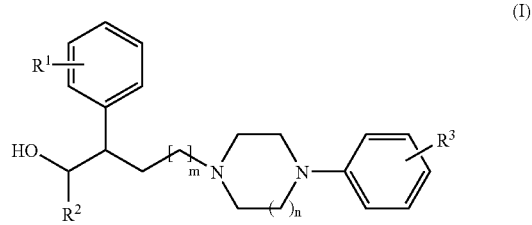

wherein:
R$^1$ represents a halogen atom,
R$^2$ represents a (C$_3$–C$_8$)-cycloalkyl group,
R$^3$ represents a (C$_1$–C$_4$)-alkoxy or (C$_1$–C$_4$)-haloalkoxy group,
m is 1 or 2, and
n is 1 or 2, and enantiomers, optical isomers, diastereomers, N-oxides (e.g., N-piperazine oxides), crystalline forms, hydrates, solvates or pharmaceutically acceptable salts thereof.

Compounds of formula I can exist as four stereoisomers, which may be present in racemic mixtures or in any other combination. Racemic mixtures can be subjected to enantiomeric enrichment, to yield compositions enriched in a particular enantiomer, or resolved completely to single enantiomers, which can be incorporated into compositions comprising single enantiomers. Enantiomeric enrichment can be expressed as ee (enantiomeric excess) as defined below.

Compounds of formula I where the carbon atom bearing the R$^1$-phenyl group has the (R) configuration are preferred. Most preferred are compounds where the carbon atom bearing the R$^1$-phenyl group has the (R) configuration and the adjacent carbon atom bearing the R$^2$ and hydroxyl groups simultaneously has the (S) configuration.

According to a preferred embodiment of the invention, R$^1$ of formula I is a fluorine atom. Further preferred is where R$^1$ is a fluorine atom at the 2-position of the phenyl ring.

The preferred cycloalkyl groups R$^2$ are those having from 3 to 6 carbon atoms, for example, cyclopropyl, cyclobutyl, cyclopentyl, and cyclohexyl groups. Further preferred are compounds wherein R$^2$ represents is an unsubstituted cyclohexyl group.

A preferred substituent that R$^3$ represents is alkoxy, more preferably methoxy and most preferably a methoxy group at position 2 of the phenyl ring.

The foregoing preferences of formula I may be present independently or in any combination.

The term "halogen" encompasses fluorine, chlorine, bromine and iodine.

The term "haloalkoxy" encompasses monohaloalkoxy groups, that is alkoxy groups substituted with one halogen substituent, and polyhaloalkoxy groups, that is alkoxy groups substituted with at least 2 halogen substituents, each of which, idependently, may be the same or different and may be attached to the same or different carbon atom(s). A preferred haloalkoxy group is 2,2,2-trifluoroethoxy.

A "metabolite" of a compound disclosed herein is a derivative of a compound which is formed when the compound is metabolized. The term "active metabolite" refers to a biologically active derivative of a compound that is formed when the compound is metabolized. The term "metabolized" refers to the sum of the processes by which a particular substance is changed in the living body. All compounds present in the body are manipulated by enzymes within the body in order to derive energy and/or to remove them from the body. Specific enzymes produce specific structural alterations to the compound. Cytochrome P450, for example, catalyzes a variety of oxidative and reductive reactions. Uridine diphosphate glucuronyltransferases, for example, catalyze the transfer of an activated glucuronic acid molecule to aromatic alcohols, aliphatic alcohols, carboxylic acids, amines and free sulphhydryl groups. Further information on metabolism may be obtained from *The Pharmacological Basis of Therapeutics*, 9*th* Edition, McGraw-Hill (1996), pages 11–17.

The metabolites of the compounds disclosed herein can be identified either by administration of compounds to a mammalian (e.g., human) host and analysis of tissue samples from the host, or by incubation of compounds with hepatic cells or other in vitro systems, such as cytochromes or microsomes, and analysis of the resulting compounds. Both methods are well known in the art.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to a member of a pair of stereoisomers whose molecules are non-superimposable mirror images of one another. As used herein, the term "optical isomer" is equivalent to the term "enantiomer". Compounds that are stereoisomers of one another, but are not enantiomers of one another, are called diastereoisomers. The terms "racemate" or "racemic mixture" refer to a mixture of equal parts of enantiomers. The term "chiral center" refers to a carbon atom to which four different groups are attached. The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E1 - E2}{E1 + E2} * 100$$

wherein E1 is the amount of the first enantiomer and E2 is the amount of the second enantiomer. Thus, if the initial ratio of the two enantiomers is 50:50, such as is present in a racemic mixture, and an enantiomeric enrichment sufficient to produce a final ratio of 50:30 is achieved, the ee with respect to the first enantiomer is 25%. However, if the final ratio is 90:10, the ee with respect to the first enantiomer is 80%. In certain embodiments, the invention provides any of the compounds set forth above having an ee of greater than zero. More preferably, the compounds have an ee of greater than about 25%, or an ee of greater than about 50%. According to further embodiments of the invention, an ee of greater than about 80% or greater than about 90% is further preferred, an ee of greater than about 95% is still further preferred and an ee of greater than about 99% is most preferred. Enantiomeric enrichment is determined by one of ordinary skill in the art using standard techniques and procedures, such as high performance liquid chromatography with a chiral column. Choice of the appropriate chiral column, eluent and conditions necessary to effect separation of the enantiomeric pair is within the knowledge of one of ordinary skill in the art. In addition, the enantiomers of compounds of formula I can be resolved by one of ordinary skill in the art using standard techniques well known in the art, such as those described by J. Jacques, et al., "Enantiomers, Racemates, and Resolutions", John Wiley and Sons, Inc., 1981. Examples of resolutions include recrystallization techniques or chiral chromatography.

Diastereoisomers differ in both physical properties and chemical reactivity. A mixture of diastercoisomers can be separated into enantiomeric pairs based on solubility, fractional crystallization or chromatographic properties, e.g., thin layer chromatography, column chromatography or HPLC.

Purification of complex mixtures of diastereoisomers into enantiomers typically requires two steps. In a first step, the mixture of diastereoisomers is resolved into enantiomeric pairs, as described above. In a second step, enantiomeric pairs are further purified into compositions enriched for one or the other enantiomer or, more preferably, resolved into compositions comprising pure enantiomers. Resolution of enantiomers typically requires reaction or molecular interaction with a chiral agent, e.g., a solvent or column matrix. Resolution of enantiomers may be achieved, for example, by converting the mixture of enantiomers, e.g., a racemic mixture, into a mixture of diastereomers by reaction with a pure enantiomer of a second agent, i.e., a resolving agent. The two resulting diastereomeric products can then be separated. The separated diastereomers are then reconverted to the pure enantiomers by reversing the initial chemical transformation.

Resolution of enantiomers can also be accomplished by differences in their non-covalent binding to a chiral substance, e.g., by chromatography on homochiral absorbants. The noncovalent binding between enantiomers and the chromatographic adsorbant establishes diastereomeric complexes, leading to differential partitioning in the mobile and bound states in the chromatographic system. The two enantiomers therefore move through the chromatographic system, e.g., column, at different rates, allowing for their separation.

Chiral resolving columns are well known in the art and are commercially available (e.g., from MetaChem Technologies Inc., a division of ANSYS Technologies, Inc., Lake Forest, Calif.). Enantiomers can be analyzed and purified, for example, using chiral stationary phases (CSPs) for HPLC. Chiral HPLC columns typically contain one form of an enantiomeric compound immobilized to the surface of a silica packing material. For chiral resolution to occur, there must be at least three points of simultaneous interaction between the CSP and one analyte enantiomer, with one or more of these interactions being stereochemically dependent.

D-phenylglycine and L-leucine are Type I CSPs and use combinations of p-p interactions, hydrogen bonds, dipole-dipole interactions, and steric interactions to achieve chiral recognition. To be resolved on a Type I column, analyte enantiomers must contain functionality complementary to that of the CSP so that the analyte undergoes essential interactions with the CSP. The sample should preferably contain one of the following functional groups: p-acid or p-base, hydrogen bond donor and/or acceptor, or an amide dipole. Derivatization is sometimes used to add the interactive sites to those compounds lacking them. The most common derivatives involve the formation of amides from amines and carboxylic acids.

The MetaChiral ODM™ is a type II CSP. The primary mechanisms for the formation of solute-CSP complexes is through attractive interactions, but inclusion complexes also play an important role. Hydrogen bonding, pi-pi, and dipole stacking are important for chiral resolution on the MetaChiral™ ODM. Derivatization is often necessary when the solute molecule does not contain the groups required for solute-column interactions. Derivatization, usually to benzylamides, is also required of some strongly polar molecules like amines and carboxylic acids, which would otherwise interact too strongly with the stationary phase through non-stereo-specific interactions.

A preferred compound of the present invention is 1-[4-cyclohexyl-4-hydroxy-3-(2-fluorophenyl)-butyl]-4-(2-methoxyphenyl)-piperazine having the formula II:

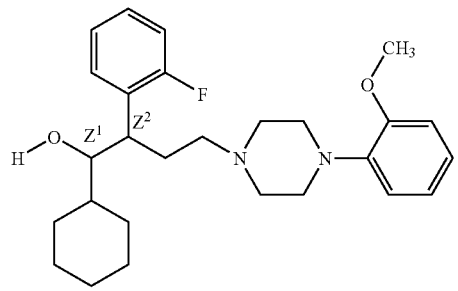

(II)

where $Z^1$ and $Z^2$ represent chiral centers. Compounds of formula II can exist in one of the following four stereoisomers:

Formula II (S,R)

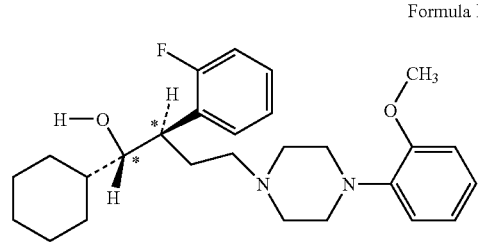

Formula II (R,S)

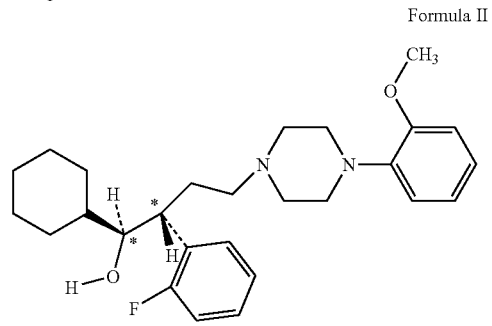

-continued

Formula II (R,R)

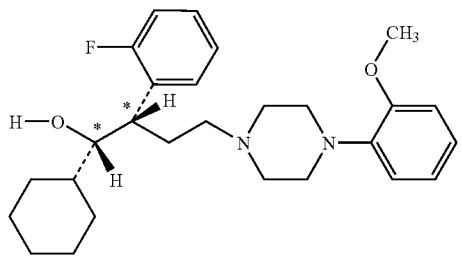

Formula II (S,S)

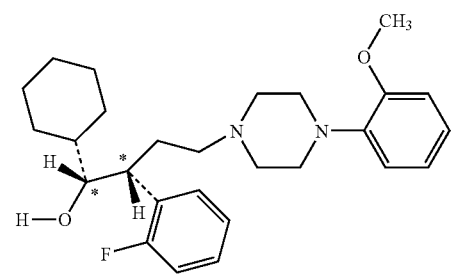

These compounds may be named as:
1-[(3R,4S)-4-cyclohexyl-4-hydroxy-3-(2-fluorophenyl)-butyl]-4-(2-methoxyphenyl)-piperazine,
1-[(3S,4R)-4-cyclohexyl-4-hydroxy-3-(2-fluorophenyl)-butyl]-4-(2-methoxyphenyl)-piperazine,
1-[(3R,4R)-4-cyclohexyl-4-hydroxy-3-(2-fluorophenyl)-butyl]-4-(2-methoxyphenyl)-piperazine, and
1-[(3S,4S)-4-cyclohexyl-4-hydroxy-3-(2-fluorophenyl)-butyl]-4-(2-methoxyphenyl)-piperazine, and enantiomers, optical isomers, diastereomers, N-oxides (e.g., N-piperazine oxides), crystalline forms, hydrates, solvates and pharmaceutically acceptable salts thereof.

Compounds of formula II can be separated into diastereomeric pairs by, for example, separation on TLC. These diastereomeric pairs are referred to herein as
diastereoisomer with upper TLC Rf; and
diastereoisomer with lower TLC Rf.

The diastereoisomers can further be enriched for a particular enantiomer or fully resolved into a single enantiomer using methods well known in the art, such as those described herein.

In another preferred embodiment, the invention provides the compound 1-[4-cyclohexyl-4-hydroxy-3-(2-fluorophenyl)-butyl]-4-[2-(2,2,2-trifluoroethoxy)-phenyl]-piperazine, which can exist in the four stereoisomers:
1-[(3R,4S)-4-cyclohexyl-4-hydroxy-3-(2-fluorophenyl)-butyl]-4-[2-(2,2,2-trifluoroethoxy)-phenyl]-piperazine,
1-[(3S,4R)-4-cyclohexyl-4-hydroxy-3-(2-fluorophenyl)-butyl]-4-[2-(2,2,2-trifluoroethoxy)-phenyl]-piperazine,
1-[(3R,4R)-4-cyclohexyl-4-hydroxy-3-(2-fluorophenyl)-butyl]-4-[2-(2,2,2-trifluoroethoxy)-phenyl]-piperazine, and
1-[(3S,4S)-4-cyclohexyl-4-hydroxy-3-(2-fluorophenyl)-butyl]-4-[2-(2,2,2-trifluoroethoxy)-phenyl]-piperazine, and enantiomers, optical isomers, diastereomers, N-oxides (e.g., N-piperazine oxides), crystalline forms, hydrates, solvates and pharmaceutically acceptable salts thereof.

3R,4S and 3R,4R are preferred. 3R,4S is most preferred.

Combination Treatments

In certain embodiments, disorders of the urinary tract are treated by administering a compound of formula I in combination with an additional 5-HT$_{1A}$ antagonist or an antagonist of one or more additional class of receptors. In preferred embodiments a compound of formula I is administered in combination with an antagonist of an α1-adrenergic, or muscarinic receptor.

In further embodiments, lower urinary tract disease is treated by administering a compound of formula I in combination with one or more inhibitor of the cyclooxygenase enzyme, which may inhibit both COX1 and COX2 isozymes or which may, alternatively, be selective for COX2 isozyme, and NO donor derivatives thereof.

Examples of antimuscarinic drugs for administration in combination with a compound of formula I are oxybutynin, tolterodine, darifenacin, and temiverine.

A compound of formula I may be administered in combination with α1-adrenergic antagonists, for the therapy of lower urinary tract symptoms, whether or not these are associated with BPH. Preferred α1-adrenergic antagonists suitable for administration in combination with a compound of formula I are, for example, prazosin, doxazosin, terazosin, alfuzosin, and tamsulosin. Additional α1-adrenergic antagonists suitable for administration in combination with a compound of formula I are described in U.S. Pat. No. 5,990,114; 6,306,861; 6,365,591; 6,387,909; and 6,403,594.

Examples of 5-$HT_{1A}$ antagonists that may be administered in combination with a compound of formula I are found in Leonardi et al., J. Pharmacol. Exp. Ther. 299: 1027–1037, 2001 (e.g., Rec 15/3079), U.S. Pat. No. 6,071,920, other phenylpiperazine derivatives described in WO 99/06383 and pending U.S. patent application Ser. Nos. 10/266,088 and 10/266,104 filed on Oct. 7, 2002. Additional 5-$HT_{1A}$ antagonists include DU-125530 and related compounds described in U.S. Pat. No. 5,462,942 and robalzotan and related compounds described in WO 95/11891.

Examples of selective COX2 inhibitors that may be administered in combination with a compound of formula I are, without limitation, nimesulide, meloxicam, rofecoxib, celecoxib, parecoxib and valdecoxib. Additional examples of selective COX2 inhibitors are described, without limitation, in U.S. Pat. No. 6,440,963. Examples of non-selective COX1–COX2 inhibitors are, without limitation, acetylsalicylic acid, niflumic acid, flufenamic acid, enfenamic acid, meclofenamic acid, tolfenamic acid, thiaprophenic acid, ibuprofen, naproxen, ketoprofen, flurbiprofen, furprofen, indomethacin, acemethacin, proglumethacin, ketorolac, diclofenac, etodolac, sulindac, fentiazac, tenoxicam, lornoxicam, cynnoxicam, ibuproxam, nabumetone, tolmetin, amtolmetin. Accordingly, each of the foregoing are non-limiting examples of COX inhibitors that may be administered in combination with a compound of formula I.

Examples of derivatives of COX inhibitors that may be administered in combination with a compound of formula I are derivatives of COX inhibitors bearing nitrate (nitrooxy) or nitrite groups, such as those given, for example, in WO 98/09948, able to release NO in vivo.

Pharmaceutical Compositions

The invention further provides pharmaceutical compositions comprising a compound of formula I or an enantiomer, diastereomer, N-oxide, crystalline form, hydrate, solvate, active metabolite or pharmaceutically acceptable salt of the compound. The pharmaceutical composition may also include optional additives, such as a pharmaceutically acceptable carrier or diluent, a flavouring, a sweetener, a preservative, a dye, a binder, a suspending agent, a dispersing agent, a colorant, a disintegrator, an excipient, a diluent, a lubricant, an absorption enhancer, a bactericide and the like, a stabiliser, a plasticizer, an edible oil, or any combination of two or more of said additives.

Suitable pharmaceutically acceptable carriers or diluents include, but are not limited to, ethanol, water, glycerol, aloe vera gel, allantoin, glycerine, vitamin-A and E oils, mineral oil, phosphate buffered saline, PPG2 myristyl propionate, magnesium carbonate, potassium phosphate, vegetable oil, animal oil and solketal.

Suitable binders include, but are not limited to, starch, gelatine, natural sugars such as glucose, sucrose and lactose, corn sweeteners, natural and synthetic gums such as acacia, ragacanth, vegetable gum, sodium alginate, carboxymethylcellulose, polyethylene glycol, waxes and the like.

Suitable disintegrators include, but are not limited to, starch such as corn starch, methyl cellulose, agar, bentonite, xanthan gum and the like.

Suitable lubricants include, but are not limited to, sodium oleate, sodium stearate, magnesium stearate, sodium benzoate, sodium acetate, sodium chloride and the like.

Suitable suspending agents include, but are not limited to, bentonite.

Suitable dispersing and suspending agents include, but are not limited to, synthetic and natural gums such as vegetable gum, tragacanth, acacia, alginate, dextran, sodium carboxymethylcellulose, methylcellulose, polyvinylpyrrolidone and gelatine.

Suitable edible oils include, but are not limited to, cottonseed oil, sesame oil, coconut oil and peanut oil.

Examples of additional additives include, but are not limited to, sorbitol, talc, stearic acid and dicalcium phosphate.

Unit Dosage Forms

The pharmaceutical composition may be formulated as unit dosage forms, such as tablets, pills, capsules, boluses, powders, granules, sterile parenteral solutions, sterile parenteral suspensions, sterile parenteral emulsions, elixirs, tinctures, metered aerosol or liquid sprays, drops, ampoules, autoinjector devices or suppositories. The unit dosage forms may be used for oral, parenteral, intranasal, sublingual or rectal administration, or for administration by inhalation or insufflation, transdermal patches, and a lyophilized composition. In general, any delivery of active ingredients that results in systemic availability of such ingredients can be used. Preferably the unit dosage form is an oral dosage form, most preferably a solid oral dosage; therefore the preferred dosage forms are tablets, pills and capsules. However, parenteral preparations are preferred too.

Solid unit dosage forms may be prepared by mixing the active agents of the present invention with a pharmaceutically acceptable carrier and any other desired additives as described above. The mixture is typically mixed until a homogeneous mixture of the active agents of the present invention is obtained and the carrier and any other desired additives are formed, i.e. the active agents are dispersed evenly throughout the composition. In this case, the composition can be formed as dry or moist granules.

Dosage forms can be formulated as, for example, "immediate release" dosage forms. "Immediate release" dosage forms are typically formulated as tablets that release at least 60%–90% of the active ingredient within 30–60 min when tested in a drug dissolution test, e.g., U.S. Pharmacopeia standard <711>. In a preferred embodiment, immediate dosage forms release at 75% of active ingredient within about 45 min.

Dosage forms can also be formulated as, for example, "controlled release" dosage forms. "Controlled," "sustained," "extended" or "time release" dosage forms are equivalent terms that describe the type of active agent delivery that occurs when the active agent is released from a delivery vehicle at an ascertainable and manipulatable rate over a period of time, which is generally on the order of minutes, hours or days, typically ranging from about sixty minutes to about 3 days, rather than being dispersed immediately upon entry into the digestive tract or upon contact with gastric fluid. A controlled release rate can vary as a function of a multiplicity of factors. Factors influencing the rate of delivery in controlled release include the particle size, composition, porosity, charge structure, and degree of hydration of the delivery vehicle and the active ingredient(s), the acidity of the environment (either internal or external to the delivery vehicle), and the solubility of the active agent in the physiological environment, i.e., the particular location along the digestive tract. Typical parameters for dissolution test of controlled release forms are found in U.S. Pharmacopeia standard <724>.

Dosage forms can, accordingly, be formulated to deliver active agent in multiphasic stages whereby a first fraction of an active ingredient is released at a first rate and at least a second fractions of active ingredient is released at a second rate. In a preferred embodiment, a dosage form can be formulated to deliver active agent in a biphasic manner, comprising a first "immediate release phase", wherein a fraction of active ingredient is delivered at a rate set forth above for immediate release dosage forms, and a second "controlled release phase," wherein the remainder of the active ingredient is released in a controlled release manner, as set forth above for controlled release dosage forms.

Tablets or pills can be coated or otherwise prepared so as to form a unit dosage form that has delayed and/or sustained action, such as controlled release and delayed release unit dosage forms. For example, the tablet or pill can comprise an inner dosage and an outer dosage component, the latter being in the form of a layer or envelope over the former. The two components can be separated by an enteric layer which serves to resist disintegration in the stomach and permits the inner component to pass intact into the duodenum or to be delayed in release.

Biodegradable polymers for controlling the release of the active agents include, but are not limited to, polylactic acid, polyepsilon caprolactone, polyhydroxybutyric acid, polyorthoesters, polyacetals, polydihydropyrans, polycyanoacrylates and crosslinked or amphipathic block copolymers of hydrogels.

For liquid dosage forms, the active substances or their physiologically acceptable salts are dissolved, suspended or emulsified, optionally with the usually employed substances such as solubilizers, emulsifiers or other auxiliaries. Solvents for the active combinations and the corresponding physiologically acceptable salts can include water, physiological salt solutions or alcohols, e.g. ethanol, propanediol or glycerol. Additionally, sugar solutions such as glucose or mannitol solutions may be used. A mixture of the various solvents mentioned may be used in the present invention too.

A transdermal dosage form is contemplated by the present invention too. Transdermal forms may be a diffusion transdermal system (transdermal patch) using either a fluid reservoir or a drug-in-adhesive matrix system. Other transdermal dosage forms include, but are not limited to, topical gels, lotions, ointments, transmucosal systems and devices, and iontophoretic (electrical diffusion) delivery systems. Transdermal dosage forms may be used for delayed release and sustained release of the active agents of the present invention.

The pharmaceutical compositions and unit dosage forms of the present invention for parenteral administration, and in particular by injection, typically include a pharmaceutically acceptable carrier, as described above. A preferred liquid carrier is vegetable oil. Injection may be, for example, intravenous, epidural, intrathecal, intramuscular, intraluminal, intratracheal or subcutaneous.

The active agents can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The active agents of the present invention may also be coupled with soluble polymers such as targetable drug carriers. Such polymers include, but are not limited to, polyvinylpyrrolidone, pyran copolymers, polyhydroxypropylmethacrylamidophenol, polyhydroxyethylaspartamidophenol, and polyethylenoxypolylysine substituted with palmitoyl residues.

Administration

The pharmaceutical composition or unit dosage forms of the present invention may be administered by a variety of routes, such as the oral and enteral, intravenous, intramuscular subcutaneous, transdermal, transmucosal (including rectal and buccal) and by inhalation routes. Preferably, the oral or transdermal route is used (i.e., with solid or liquid formulations or skin patches).

The pharmaceutical composition or unit dosage forms comprising an effective amount of the present invention may be administered to an animal, preferably a human, in need of treatment of neuromuscular dysfunction of the lower urinary tract as described by E. J. McGuire in "Campbell's UROLOGY", 5$^{th}$ Ed. 616–638, 1986, W.B. Saunders Company, and patients affected by any physiological dysfunction related to impairment of 5-HT$_{1A}$ receptor function. Such dysfunctions include, without limitation, central-nervous-system disorders such as depression, anxiety, eating disorders, sexual dysfunction, addiction and related problems.

As used herein, the term "effective amount" refers to an amount that results in measurable amelioration or favorable change of at least one symptom, marker, or parameter of a specific disorder. In a preferred embodiment, the compound treats disorders of the urinary tract, such as urinary urgency, overactive bladder, increased urinary frequency, reduced urinary compliance (reduced bladder storage capacity), cystitis (including interstitial cystitis), incontinence, urine leakage, enuresis, dysuria, urinary hesitancy and difficulty in emptying the bladder, or central nervous system disorders due to serotonergic dysfunction (such as anxiety, depression, hypertension, sleep/wake cycle disorders, feeding behaviour, sexual function and cognition disorders in mammals (particularly a human) associated to stroke, injury, dementia and due to neurological development, disorders from hyperactivity related to an attention deficit (ADHD), drug addiction, drug withdrawal, irritable bowel syndrome.

The pharmaceutical composition or unit dosage form of the present invention may be administered according to a dosage and administration regimen defined by routine testing in the light of the guidelines given above in order to obtain optimal activity while minimizing toxicity or side effects for a particular patient. However, such fine tuning of the therapeutic regimen is routine in the light of the guidelines given herein.

The dosage of the active agents of the present invention may vary according to a variety of factors such as underlying disease conditions, the individual's condition, weight, sex and age, and the mode of administration. An effective amount for treating a disorder can easily be determined by empirical methods known to those of ordinary skill in the art, for example by establishing a matrix of dosages and frequencies of administration and comparing a group of experimental units or subjects at each point in the matrix. The exact amount to be administered to a patient will vary depending on the state and severity of the disorder and the physical condition of the patient. A measurable amelioration of any symptom or parameter can be determined by a person skilled in the art or reported by the patient to the physician. It will be understood that any clinically or statistically significant attenuation or amelioration of any symptom or parameter of urinary tract disorders is within the scope of the invention. Clinically significant attenuation or amelioration means perceptible to the patient and/or to the physician.

For example, a single patient may suffer from several symptoms of dysuria simultaneously, such as, for example, urgency and excessive frequency of urination or both, and these may be reduced using the methods of the present invention. In the case of incontinence, any reduction in the frequency or volume of unwanted passage of urine is considered a beneficial effect of the present method of treatment.

The amount of the agent to be administered can range between about 0.01 and about 25 mg/kg/day, preferably between about 0.1 and about 10 mg/kg/day and most preferably between 0.2 and about 5 mg/kg/day. It will be understood that the pharmaceutical formulations of the present invention need not necessarily contain the entire amount of the agent that is effective in treating the disorder, as such effective amounts can be reached by administration of a plurality of doses of such pharmaceutical formulations.

In a preferred embodiment of the present invention, the compounds are formulated in capsules or tablets, preferably containing 50 to 200 mg of the compounds of the invention, and are preferably administered to a patient at a total daily dose of 50 to 400 mg, preferably 150 to 250 mg and most preferably about 200 mg, for relief of urinary incontinence and dysfunctions under treatment with 5-$HT_{1A}$ receptor ligand. Total daily dosages may be administered through plural administration, e.g., 4 sub-dosages, per day. In a preferred embodiments the total daily dosage is administered in 1 or 2 dosages per day.

A pharmaceutical composition for parenteral administration contains from about 0.01% to about 100% by weight of the active agents of the present invention, based upon 100% weight of total pharmaceutical composition.

Generally, transdermal dosage forms contain from about 0.01% to about 100% by weight of the active agents versus 100% total weight of the dosage form.

The pharmaceutical composition or unit dosage form may be administered in a stingle daily dose, or the total daily dosage may be administered in divided doses. In addition, co-dministration or sequential administration of another compound for the treatment of the disorder may be desirable. Examples of such combination treatments are set forth above.

For combination treatment where the compounds are in separate dosage formulations, the compounds can be administered concurrently, or each can be administered at separate staggered times. For example, the compound of the invention may be administered in the morning and the antimuscarinic compound may be administered in the evening, or vice versa. Additional compounds may be administered at specific intervals too. The order of administration will depend upon a variety of factors including age, weight, sex and medical condition of the patient; the severity and aetiology of the disorders to be treated, the route of administration, the renal and hepatic function of the patient, the treatment history of the patient, and the responsiveness of the patient. Determination of the order of administration may be-fine-tuned and such fine-tuning is routine in the light of the guidelines given herein.

Uses-Methods for Treatment

Without wishing to be bound by theory, it is believed that administration of 5-$HT_{1A}$ receptor antagonists decreases or prevents unwanted activity of the sacral reflex and/or cortical mechanisms that control micturition. Thus, it is contemplated that a wide range of neuromuscular dysfunctions of the lower urinary tract can be treated using the compounds of the present invention, including without limitation dysuria, incontinence and enuresis (overactive bladder). Dysuria includes urinary frequency, nocturia, urgency, reduced urinary compliance (reduced bladder storage capacity), difficulty in emptying the bladder, i.e., a suboptimal volume of urine is expelled during micturition. Incontinence syndromes include stress incontinence, urgency incontinence and enuresis incontinence, as well as mixed forms of incontinence. Enuresis refers to the involuntary passage of urine at night or during sleep.

The compounds of the present invention may also be useful for the treatment of central nervous system disorders due to serotonergic dysfunction.

SYNTHESIS OF THE COMPOUNDS OF THE INVENTION

The compounds of the invention are generally prepared according to the following schemes:

Scheme 1

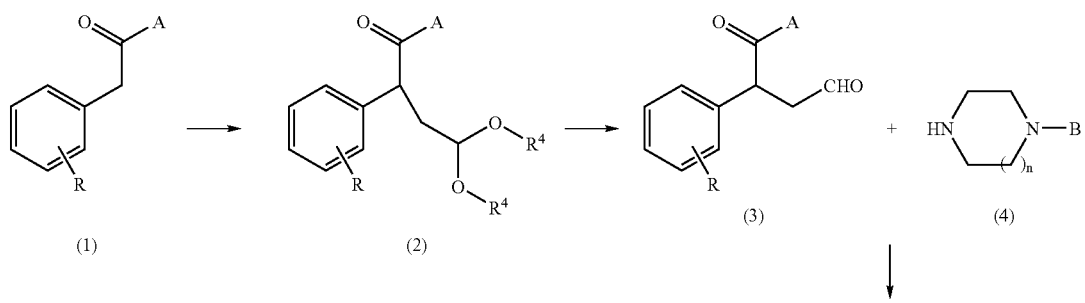

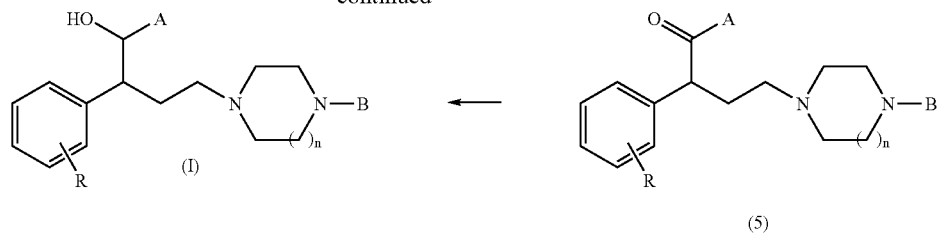

Groups A and R are the same as $R^2$ and $R^1$ as defined with reference to the general formula (I). Group B is equivalent to the group $R^3$-phenyl as defined with reference to the general formula (I). $R^4$ represents alkyl.

Starting material (1) is treated with a base, preferably potassium tert-butoxide, followed by alkylation with 2-bromomethylacetaldehyde dialkyl acetal or other carbonyl protected 2-haloacetaldehyde (e.g., the $R^4$ alkyl groups can also be joined in a cycle to give a dioxolane or dioxane ring). Other alternative and appropriate bases to carry out the condensation include lithium amides, sodium hydride, sodium hydroxide, potassium hydroxide, potassium carbonate, cesium carbonate and the like with the aid or not of phase transfer catalysts.

The reaction is preferably carried out in a solvent such as dimethyl sulfoxide or toluene at a temperature of 0° C. to reflux.

Treatment of (2) with an acid, such as hydrochloric acid or p-toluene-sulfonic acid or trifluoroacetic acid in a suitable organic solvent, achieves aldehyde (3). Generally, the reaction is conducted in a protic solvent, such a mixture of aqueous acid and acetone or tetrahydrofuran, at temperatures of from about 5° to 75° C. preferably at ambient temperature. A preferred and alike method consists of carrying out the reaction in a mixture of aqueous trifluoroacetic acid in a chlorinated solvent at ambient temperature.

Aldehyde (3) is coupled with the desired aryl diazocycloalkane (4) by reductive amination procedure to prepare (5). The reaction is preferably conducted at ambient temperature in a non-reactive solvent such as dichloroethane or methylene chloride or chloroform in the presence of sodium triacetoxyborohydride and is substantially complete in one to 24 hours (see for example A. F. Abdel-Magid, et al., J. Org. Chem., 61, 3849 (1996)) or it can be conducted in a protic solvent (e.g., methanol) with the aid of sodium cyanoborohydride, optionally in the presence of molecular sieves.

Reduction of (5) to the alcohol (I) is readily accomplished using a reducing agent such as sodium borohydride or, diisobutylaluminum hydride or other aluminum or boron hydride or other reduction method to carry out the conversion ketone to alcohol very well known to those skilled in the art, to prepare the hydroxy compound (I). The reaction is preferably conducted in an organic solvent such as methanol or methylene chloride or tetrahydrofuran at temperatures of from about −20° C. to ambient temperature.

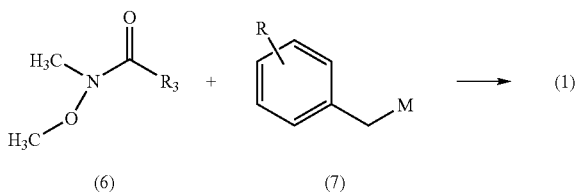

Starting material (1) is either commercially available or can be prepared by coupling the proper Weinreb amide (6) (See Nahm and Weinreb, Tetrahedron Lett., 22, 3815, (1981)) with (7), as described in Scheme 2 above, where M is a metallic salt, such as lithium or magnesium halide.

The reaction is preferably conducted under an inert atmosphere preferably nitrogen, in an aprotic solvent, such as tetrahydrofuran, at ambient or lower temperatures down to −78° C.

Alternatively, an ester of structure ACOOalkyl can be treated with a substituted benzylmagnesium chloride or benzylmagnesium bromide under standard conditions well known in the art to provide the ketone of structure (1).

Preferred and alike way of synthesis of (1) is the palladium catalyzed coupling of an acyl halide with a compound (7) where M is Zn halide.

More specifically, the compounds of formula (5) can be prepared following the procedure described in Scheme 3. All substituents, unless otherwise indicated, are as defined previously. The reagents and starting materials are readily available to one of ordinary skill in the art.

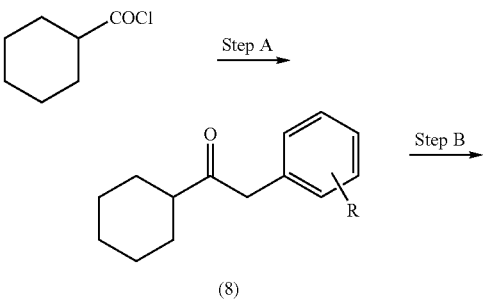

-continued

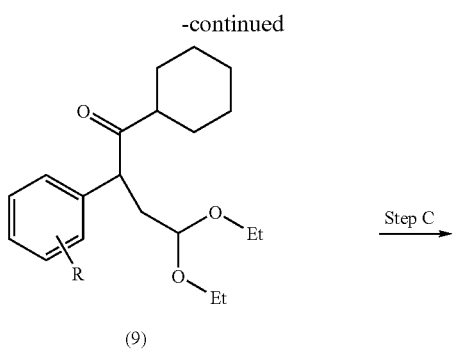

(9)

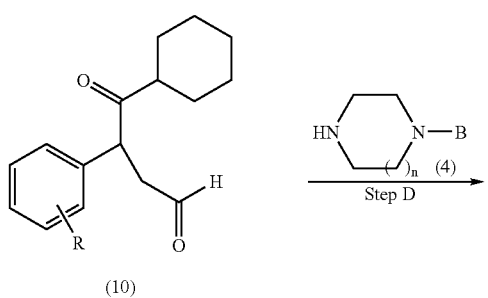

(10)

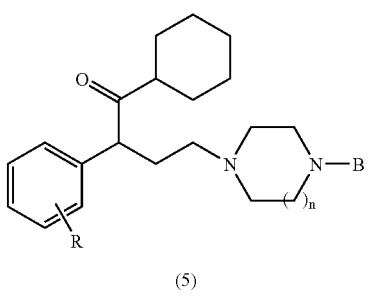

(5)

In Scheme 3, step A, for example, cyclohexanecarbonyl chloride is added to a mixture of the suitable benzylzinc chloride or bromide and a proper palladium catalyst, e.g., dichlorobis(triphenylphosphine)palladium(II) stirred at 0° C. in a solvent such as tetrahydrofuran. Afterwards, stirring is continued at ambient temperature for 4–24 h. Then the reaction is quenched for example with an aqueous saturated solution of ammonium chloride. Usual work-up procedure by extraction provide the ketone (8). Ketone (8) can be purified by techniques well known in the art, such as flash chromatography on silica gel with a suitable eluent, such as ethyl acetate/hexane to provide the purified material. Alternatively, the crude ketone (8) can be carried on to step B.

In Scheme 3, step B, ketone (8) is alkylated with bromoacetaldehyde diethyl acetal under conditions well known in the art to provide compound of structure (9). For example, ketone (8) is dissolved in a suitable organic solvent, such as dimethyl sulfoxide or toluene and treated with a slight excess of a suitable base, such as potassium tert-butoxide. The reaction is stirred for about 15 to 30 minutes at a temperature of between 0° C. and the reflux temp. of the solvent and bromoacetaldehyde diethyl acetal is added dropwise to the reaction. One of ordinary skill in the art would readily appreciate that bromoacetaldehyde dimethyl acetal, bromoacetaldehyde ethylene acetal and the like may be used in place of the corresponding diethyl acetal.

In Scheme 3, step C, compound (9) is hydrolyzed under acidic conditions to provide aldehyde (10) in a manner analogous to the procedure described in Scheme I. More specifically, for example, compound (9) is dissolved in a suitable organic solvent, such as dichloromethane and treated with a suitable acid, such as aqueous trifluoroacetic acid. The reaction mixture is stirred for about 1 to 6 hours at room temperature. The reaction mixture is then diluted with the same solvent, washed with brine, the organic layer is separated, dried over anhydrous sodium sulfate, filtered and concentrated under vacuum to provide aldehyde (10). Aldehyde (10) can be purified by techniques well known in the art, such as flash chromatography on silica gel with a suitable eluent, such as ethyl acetate/hexane. Alternatively, crude aldehyde (10) can be used directly in step D.

In Scheme 3, step D, aldehyde (10) is reductively aminated, under conditions well known in the art, with diazocycloalkane (4) to provide the ketone (5) in a manner analogous to the procedure described in Scheme I. More specifically, for example, aldehyde (10) is dissolved in a suitable organic solvent, such as methylene chloride. To this solution is added about 1.05 or more equivalents of diazocycloalkane (4). Acetic acid may optionally be added to aid in dissolution of the diazocycloalkane (4). Then about 1.4 to 1.5 equivalents of sodium triacetoxyborohydride is added and the reaction is stirred at room temperature for about 3 to 5 hours. The reaction is then quenched by addition of a suitable base, such as aqueous sodium carbonate or hydroxide to provide a pH of about 8 to about 12. The quenched reaction is then extracted with a suitable organic solvent, such as methylene chloride. The organic extracts are combined, washed with brine, dried, filtered and concentrated under vacuum to provide the compound of formula (5). This material can then be purified by techniques well known in the art, such as flash chromatography on silica gel with a suitable eluent, such as ethyl acetate/petroleum ether or hexane.

Scheme 4

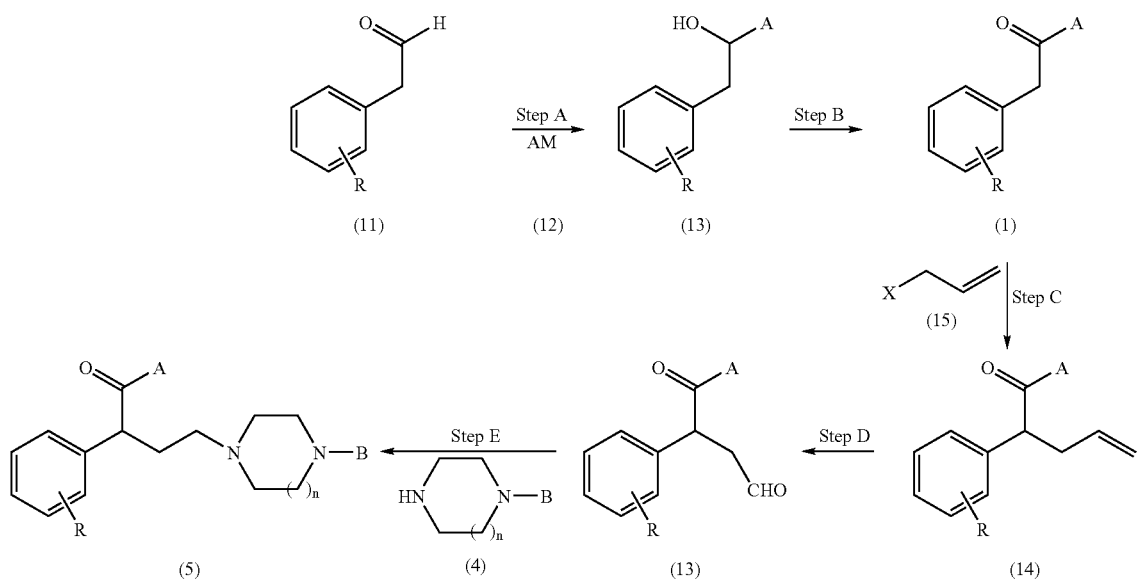

Alternatively, compounds of structure (5) can be prepared following the procedure described in Scheme 4. All substituents, unless otherwise indicated, are as defined previously. The reagents and starting materials are readily available to one of ordinary skill in the art.

In Scheme 4, step A, aldehyde (11) is combined with a suitable organometallic reagent (12) under conditions well known in the art to provide alcohol (13). Examples of suitable organometallic reagents include Grignard Reagents, alkyl lithium reagents, alkyl zinc reagents, and the like. Grignard Reagents are preferred. For examples of typical Grignard Reagents and reaction conditions, see J. March, "Advanced Organic Chemistry: Reactions, Mechanisms, and Structure", 2nd Edition, McGraw-Hill, pages 836–841 (1977). More specifically, aldehyde (11) is dissolved in a suitable organic solvent, such as tetrahydrofuran or toluene, cooled to about −5° C. and treated with about 1.1 to 1.2 equivalents of a Grignard reagent of formula (12) wherein M is MgCl or MgBr. The reaction is stirred for about 0.5 to 6 hours, then quenched, and alcohol (13) is isolated by well-known work-up procedure.

In Scheme 4, step B, alcohol (13) is oxidized under standard conditions well know in the art, such as those described by J. March, "Advanced Organic Chemistry: Reactions, Mechanisms, and Structure", 2nd Edition, McGraw-Hill, pages 1082–1084 (1977), to provide ketone (1). [Ketone (1) is the starting material used in Scheme 1 above.]

For example, the above oxidation is also performed using standard Swern Oxidation conditions which are well known to one of ordinary skill in the art (Marx, Tidwell-J. Org. Chem. 49, 788, 1984) or the alcohol (13) is dissolved in a suitable organic solvent, such as methylene chloride, the solution cooled with a wet ice-acetone bath, and treated with 2.5 to 3.0 equivalents of dimethyl sulfoxide. After stirring for about 30 minutes, the reaction is then treated with about 1.8 equivalents of $P_2O_5$. The reaction is stirred for about 3 hours and then, preferably, treated over about 30 minutes with about 3.5 equivalents of a suitable amine, such as triethylamine. The cooling bath is then removed and the reaction is stirred for about 8 to 16 hours. The ketone (1) is then isolated by standard extraction techniques well known in the art.

In Scheme 4, step C, ketone (1) is treated with a suitable base followed by addition of the alkene (15), wherein X is a suitable leaving group, to provide compound (14). For example, ketone (1) is combined with an excess of alkene (15) in a suitable organic solvent, such as tetrahydrofuran, and cooled with a wet ice acetone bath. Examples of suitable leaving groups are Cl, Br, I, tosylate, mesylate, and the like. Preferred leaving groups are Cl and Br. About 1.1 equivalents of a suitable base is added and the reaction is allowed to stir for about 2 hours at room temperature. Examples of suitable bases are potassium tert-butoxide, sodium hydride, $NaN(Si(CH_3)_3)_2$, lithium diisopropyl amide, $KN(Si(CH_3)_3)_2$, $NaNH_2$, sodium ethoxide, sodium methoxide and the like. Potassium tert-butoxide is the preferred suitable base. The reaction is then quenched with aqueous acid and compound (14) is isolated by usual work-up procedure.

In Scheme 4, step D, compound (14) is treated with a suitable oxidizing agent to provide aldehyde (3). (Aldehyde (3) is also prepared in Scheme 1.) Examples of suitable oxidizing agents are ozone, $NaIO_4$/Osmium catalyst, and the like. Ozone is the preferred oxidizing agent. Examples of suitable oxidizing reagents and conditions are described by J. March, "Advanced Organic Chemistry: Reactions, Mechanisms, and Structure", 2nd Edition, McGraw-Hill, pages 1090–1096 (1977).

For example, compound (14) is dissolved in a suitable organic solvent, such as methanol, a small amount of Sudan III is added, and the solution is cooled to about −20° C. Ozone is bubbled into the solution for about 4 hours until the pink color turns to a pale yellow color. Then a reducing agent such as $Me_2S$ or tributylphosphine is added. Concentration provides the intermediate dimethyl acetal of aldehyde (3). This dimethyl acetal is readily hydrolyzed under standard acidic conditions to provide aldehyde (3). Alternatively, direct acidic work-up of the crude reaction mixture provides aldehyde (3). Alternatively, aldehyde (3) can be obtained directly by ozonolysis of (14) in a non-acetal forming solvent, such as methylene chloride.

In Scheme 4, step E, aldehyde (3) is reductively aminated under conditions analogous to those described above in Scheme 3, step D, to provide compound (5). (Compound 5 is also prepared in Scheme I.)

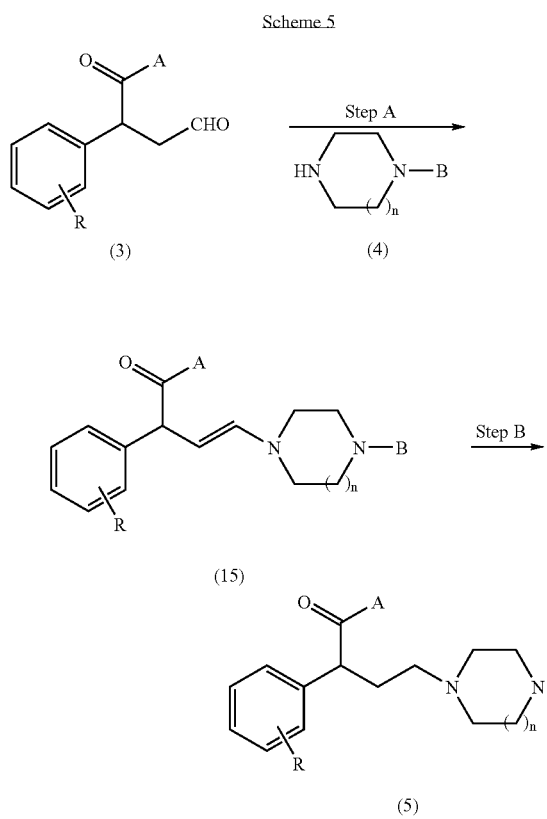

Scheme 5 provides an alternative synthesis for the preparation of ketone (5). All substituents, unless otherwise indicated, are as defined previously. The reagents and starting materials are readily available to one of ordinary skill in the art.

In Scheme 5, step A, aldehyde (3) is condensed with diazocycloalkane (4) under standard conditions well known in the art to provide the enamine (15). For example, about 1.05 equivalents of aldehyde (3) dissolved in a suitable organic solvent, such as isopropyl acetate or isopropanol, is added to neat diazocycloalkane (4), free base. Additional organic solvent is added to produce a slurry and the reaction is stirred for about 1 to 2 hours. The enamine (15) is then isolated by standard techniques, such as collection by filtration.

In Scheme 5, step B, the enamine (15) is hydrogenated under conditions well known to one of ordinary skill in the art to provide compound (5). For example, enamine (15) is combined with a suitable organic solvent, such as isopropyl alcohol and a catalytic amount of 5% palladium on carbon in a Parr bottle. The mixture is placed under 50 psi (344850 pascals) of hydrogen and shaken for about 2 days at room temperature. The slurry is then filtered to remove catalyst and the filtrate is concentrated to provide compound (5).

Whichever the way they are prepared, the keto intermediates (5) can be transformed into the corresponding final compounds of formula I by reaction with reducing agents, in particular those generating hydrogen anions, such as sodium borohydride or DIBAL-H.

Such keto intermediates (5), reduced without previous resolution, in general generate a mixture of diastereoisomers where the couple (RS,SR) is quantitatively predominant over the (RR,SS) couple. The (RS,SR) couple is then isolated by column chromatography on silica gel and resolved into the single (RS) and (SR) enantiomers by, for instance, chromatography on chiral stationary phase or by other methods well known to those skilled in the art.

Alternatively, the racemic ketone (5) may be resolved into its two enantiomers by known methods and the (R)-5 is then submitted to reduction generating preferentially the (S,R) enantiomer, that is the preferred one of this invention, and can be easily purified by physical methods.

Stereochemistry

In Scheme 1, compounds I are obtained in syn/anti mixture of diastereoisomers with ratio depending on the reaction condition used. The diastereoisomers can be separated by usual techniques known to those skilled in the art including fractional crystallization of the bases or their salts or chromatographic techniques such as LC or flash chromatography. For both of the diastereoisomers, the (+) enantiomer can be separated from the (−) enantiomer using techniques and procedures well known in the art, such as that described by J. Jacques, et al., "Enantiomers, Racemates, and Resolutions", John Wiley and Sons, Inc., 1981. For example, chiral chromatography with a suitable organic solvent, such as ethanol/acetonitrile and Chiralpak AD packing, 20 micron can also be utilized to effect separation of the enantiomers.

The free bases of formula I, their diastereoisomers or enantiomers can be converted to the corresponding pharmaceutically acceptable salts under standard conditions well known in the art. For example, the free base of formula I is dissolved in a suitable organic solvent, such as methanol, treated with one equivalent of maleic or oxalic acid for example, one or two equivalents of hydrochloric acid or methanesulphonic acid for example, and then concentrated under vacuum to provide the corresponding pharmaceutically acceptable salt. The residue can then be purified by recrystallization from a suitable organic solvent or organic solvent mixture, such as methanol/diethyl ether.

The N-oxides of compounds of formula I can be synthesized by simple oxidation procedures well known to those skilled in the art. The oxidation procedure described by P. Brougham et al. (*Synthesis*, 1015–1017, 1987), allows the two nitrogen of the piperazine ring to be differentiated, enabling both the N-oxides and N,N'-dioxide to be obtained.

The following examples represent typical syntheses of the compounds of Formula I as described generally above. These examples are illustrative only and are not intended to limit the invention in any way. The reagents and starting materials are readily available to one of ordinary skill in the art.

EXAMPLE 1

1-[(SR-RS)-4-cyclohexyl-4-hydroxy-3-(2-fluorophenyl)-butyl]-4-(2-methoxyphenyl)-piperazine (diastereoisomer with upper TLC Rf) (Ex. 1)

1-[(3S,4R)-4-cyclohexyl-4-hydroxy-3-(2-fluorophenyl)-butyl]-4-(2-methoxyphenyl)-piperazine (Ex. 1X)

1-[(3R,4S)-4-cyclohexyl-4-hydroxy-3-(2-fluorophenyl)-butyl]-4-(2-methoxyphenyl)-piperazine (Ex. 1Y)

EXAMPLE 2

1-[(RR-SS)-4-cyclohexyl-4-hydroxy-3-(2-fluorophenyl)-butyl]-4-(2-methoxyphenyl)-piperazine (diastereoisomer with lower TLC Rf) (Ex. 2)

1-[(3R,4R)-4-cyclohexyl-4-hydroxy-3-(2-fluorophenyl)-butyl]-4-(2-methoxyphenyl)-piperazine (Ex. 2X)

1-[(3S,4S)-4-cyclohexyl-4-hydroxy-3-(2-fluorophenyl)-butyl]-4-(2-methoxyphenyl)-piperazine (Ex. 2Y)

Cyclohexyl 2-fluorobenzyl ketone (Compound 1a)

To a mixture of 36 ml of 2-fluorobenzylzinc chloride (0.5 M sol. in tetrahydrofuran) and 0.008 g of dichlorobis(triphenylphosphine)palladium(II) stirred at 0° C. was added dropwise via a syringe 2.14 ml of cyclohexanecarbonyl chloride. Afterwards, the reaction mixture was stirred at r.t. for 4 h, quenched with an aqueous saturated solution of ammonium chloride (25 ml), extracted with 20 ml of EtOAc, which was dried ($Na_2SO_4$) and evaporated to dryness in vacuo affording 3.52 g of the title compound as a crude, which could be used in the following step without further purification.

$^1$H-NMR ($CDCl_3$, δ): 1.10–2.05 (m, 10H), 2.47 (tt, 1H), 3.77 (s, 2H), 6.97–7.32 (m, 4H)

4-Cyclohexyl-4-oxo-3-(2-fluorophenyl)-butyraldehyde diethyl acetal (Compound 1b)

A solution of 5.02 g of compound 1a in 136 ml of toluene was heated at reflux recovering 35 ml of toluene by distillation to remove water. Afterwards, 3.18 g of potassium tert-butoxide was added and stirring at reflux was continued for 30 min; the reaction mixture was cooled to 80° C. and 4.27 ml of 2-bromoacetaldehyde diethyl acetal was added. After 18 h at reflux, the reaction mixture was cooled to r.t., quenched with an aqueous saturated solution of ammonium chloride (30 ml) and extracted with 30 ml of EtOAc. The extracts were dried ($Na_2SO_4$) and evaporated to dryness in vacuo giving a crude which was purified by flash chromatography (petroleum ether-EtOAc 92.5:7.5) affording 2.97 g of the pure title product.

$^1$H-NMR ($CDCl_3$, δ): 1.00–2.10 (m, 17H), 2.20–2.52 (m, 2H), 3.30–3.72 (m, 4H), 4.25–4.45 (m, 2H), 6.90–7.35 (m, 4H)

4-Cyclohexyl-4-oxo-3-(2-fluorophenyl)-butyraldehyde (Compound 1c)

A mixture of 1.12 g of the compound 1b, 9 ml of 50% aqueous trifluoroacetic acid and 18 ml of $CH_2Cl_2$ was stirred for 2 h at r.t., and then diluted with 10 ml of $CH_2Cl_2$. The organic layer was separated, washed with brine (2×15 ml), dried ($Na_2SO_4$) and evaporated to dryness in vacuo to afford a crude (0.88 g), used in the next step without further purification.

$^1$H-NMR ($CDCl_3$, δ): 0.90–2.10 (m, 10H), 2.25–2.70 (m, 2H), 3.12–3.52 (m, 1H), 4.60–4.80 (m, 1H), 6.95–7.40 (m, 4H), 9.75 (s, 1H)

1-[4-cyclohexyl-4-oxo-3-(2-fluorophenyl)-butyl]-4-(2-methoxyphenyl)-piperazine (Compound 1d)

A mixture of 0.88 g of the compound 1c, 0.84 g of 1-(2-methoxyphenyl)piperazine.HCl, 1.06 g of sodium triacetoxyborohydride and 33 ml of $CH_2Cl_2$ was stirred at r.t. for 1 h, kept overnight resting, alkalinised with 20% aqueous $Na_2CO_3$ The organic layer was separated, washed with brine (2×30 ml), dried ($Na_2SO_4$) and evaporated to dryness in vacuo the give a crude (1.46 g) which was used in the next step without further purification. A sample was purified by flash chromatography (petroleum ether-EtOAc 6:4) affording a pure sample.

$^1$H-NMR ($CDCl_3$, δ): 1.05–2.00 (m, 11H), 2.20–2.44 (m, 4H), 2.45–2.72 (m, 4H), 2.90–3.20 (m, 4H), 3.85 (s, 3H), 4.38 (t, 1H), 6.80–7.30 (m, 8H)

(SR,RS)-1-Cyclohexyl-4-[4-(2-methoxyphenyl)piperazin-1-yl]-2-(2-fluorophenyl)butan-1-ol (Diastereoisomer with Upper TLC Rf) and (RR,SS)-1-Cyclohexyl-4-[4-(2-methoxyphenyl)piperazin-1-yl]-2-(2-fluorophenyl)butan-1-ol (diastereoisomer with Lower TLC Rf)

To a solution of 1.46 g of the compound 1d in 33 ml of methanol stirred at 0° C. was added 0.19 g of sodium borohydride and the mixture was stirred at r.t. for 4 h. The solvent was evaporated and the reaction crude was taken up with water and extracted with EtOAc. The organic layer was separated, washed with brine (2×15 ml), dried ($Na_2SO_4$) and evaporated to dryness in vacuo to give a crude which was purified by sequential flash chromatography (petroleum ether-EtOAc-2 N ammonia in methanol 75:25:2; petroleum ether-EtOAc-2 N ammonia in methanol 80:20:2) affording 0.82 g of the compound of Example 1 (upper TLC Rf; eluent: petroleum ether-EtOAc-2 N ammonia in methanol 70:30:2) followed by 0.062 g of the compound of Example 2 (lower TLC Rf; same eluent).

Ex. 1: $^1$H-NMR ($CDCl_3$, δ): 0.80–1.40 (m, 6H), 1.50–1.82 (m, 4H), 1.85–2.10 (m, 3H), 2.21–2.45 (m, 2H), 2.52–2.85 (m, 4H), 2.98–3.26 (m, 4H), 3.28–3.42 (m, 1H), 3.50–3.60 (m, 1H), 3.85 (s, 3H), 6.80–7.30 (m, 7H), 7.62–7.80 (m, 1H); OH peak not detectable Ex. 2: $^1$H-NMR ($CDCl_3$, δ): 0.75–2.00 (m, 13H), 2.00–2.30 (m, 1H), 2.31–2.55 (m, 2H), 2.56–2.95 (m, 4H), 3.00–3.30 (m, 4H and OH), 3.60 (dd, 1H), 3.85 (s, 3H), 6.80–7.38 (m, 8H)

1-[(3S,4R)-4-cyclohexyl-4-hydroxy-3-(2-fluorophenyl)-butyl]-4-(2-methoxyphenyl)-piperazine (Example 1X)

This compound was obtained by chiral column chromatography on the compound of Example 1 using Chiralpak AD (0.46×25 cm), eluting with n-hexane-EtOH 95:5 (flow=0.5 ml/min; detector UV 247 nm).

1-[(3R,4S)-4-cyclohexyl-4-hydroxy-3-(2-fluorophenyl)-butyl]-4-(2-methoxyphenyl)-piperazine (Example 1Y)

This compound was obtained by chiral column chromatography on the compound of Example 1 using Chiralpak AD (0.46×25 cm), eluting with n-hexane-ethanol 95:5 (flow=0.5 ml/min; detector UV 247 nm).

1-[(3R,4R)-4-cyclohexyl-4-hydroxy-3-(2-fluorophenyl)-butyl]-4-(2-methoxyphenyl)-piperazine (Example 2X)

This compound was obtained by chiral column chromatography on the compound of Example 2 using Chiralpak AD (2×25 cm), eluting with n-hexane-ethanol 85:15 (flow=8 ml/min; detector UV 254 nm).

1-[(3S,4S)-4-cyclohexyl-4-hydroxy-3-(2-fluorophenyl)-butyl]-4-(2-methoxyphenyl)-piperazine (Example 2Y)

This compound was obtained by chiral column chromatography on the compound of Example 2 using Chiralpak AD (2×25 cm), eluting with n-hexane-ethanol 85:15 (flow=8 ml/min; detector UV 254 nm).

The absolute stereochemistry of compounds 1X and 2Y, in form of their salts with hydrogen bromide, was determined by single crystal x-ray diffraction, as follows.

Single crystal X-ray diffraction experiment:

A needle shape single crystal was selected for X-ray diffraction analysis and mounted on a glass fiber. The data were collected on Rigaku Rapid cylinder shape image plate X-ray area detector with detector aperture=45.0×25.6 cm. It was controlled by a Windows 200Q based PC computer with Rapid Auto version 1.06 software (Rigaku, 2000), at low temperature (−120° K), with Micromax-002 micro-Confocal mirrors CuKaradiation [λ(CuKa)=1.5405 Å]. Indexing was performed from three 30 oscillations frames that were exposed for 360 seconds. All reflections were measured in five image groups with six frames in each group; the exposure time was 160 seconds per degree. Among them, five groups of images were at angles phi=0°, 90°, 180°, 270° with chi=50° and phi=0° with chi=0° all frames were delta omega=30°, and which makes the 2θmax=136.3°. The sample/detector distance was 12.74 cm. The data reduction program, Rapid Auto version 1.06 (Rigaku, 2000), determined the Laue group was −1, and total 7,986 reflections were integrated for structure solution and refinements.

Single Crystal Results:

The structure was solved by direct methods, using SIR92 (Altomare et al. 1994). All calculations were performed using the Crystal Structure 3.0 (MSC/Rigaku, 2002; Watkin et al., 1996, Carruthers and Watkin, 1979) crystallographic software package. The trial solution obtained 38 nohydrogen atoms in the asymmetrical unit. Least squares refinement included all nonhydrogen atomic coordinates and anisotropic thermal parameters. The final cycle of full-matrix least-squares refinement on F was based on 6,297 reflections with I>3σ(I), converged with agreement factors: R=0.071, S=2.224, Rw=0.073. The absolute configuration was determined by using the calculated Flack×parameter, which was 0.00 with esd=0.04. Expected values are 0.0 (within 3 esd's) for correct and +1.0 for inverted absolute structure.

REFERENCES

Altomare, A., Cascarano, G., Giacovazzo, C. Guagliardi, A., Burla, M., Polidori, G., and Camalli, M., (1994) SIR92, J. Appl. Cryst., 27, 435.

Carruthers, J. R. and Watkin, D. J. (1979), Acta Cryst, A35, 698–699.

Rigaku (2000), Rapid Auto, Rigaku Corporation, Tokyo, Japan.

Rigaku and Rigaku/MSC, (2000–2002), Crystal Structure Analysis Software, Crystal Structure Version 3.00, Rigaku/MSC, 9009 New Trails Drive, The Woodlands, Tex., USA 77381–5209. Rigaku, 3–9–12 Akishima, Tokyo 196–8666, Japan.

Watkin, D. J., Prout, C. K. Carruthers, J. R. & Betteridge, P. W., CRYSTALS Issue 10, Chemical Crystallography Laboratory, Oxford, UK.

EXAMPLE 3

1-[(RS,SR)-4-cyclohexyl-4-hydroxy-3-(2-fluorophenyl)-butyl]-4-[2-(2,2,2-trifluoroethoxy)-phenyl]-piperazine (Diastereoisomer with Upper TLC Rf)

EXAMPLE 4

1-[(RR,SS)-4-cyclohexyl-4-hydroxy-3-(2-fluorophenyl)-butyl]-4-[2-(2,2,2-trifluoroethoxy)-phenyl]-piperazine (Diastereoisomer with Lower TLC Rf)

1-[4-cyclohexyl-4-oxo-3-(2-fluorophenyl)-butyl]-4-[2-(2,2,2-trifluoroethoxy)-phenyl]-piperazine (Compound 3a)

The title compound was prepared following the procedure described for the compound 1d but using 1-(2,2,2-trifluoroethoxyphenyl)-piperazine.HCl instead of 1-(2-methoxyphenyl)-piperazine.HCl. Purification by flash chromatography (petroleum ether-EtOAc 7:3) afforded the title compound (51%).

$^1$H-NMR (CDCl$_3$, δ): 1.00–1.85 (m, 10H), 1.86–2.05 (m, 1H), 2.20–2.44 (m, 4H), 2.45–2.70 (m, 4H), 2.95–3.18 (m, 4H), 4.25–4.60 (m, 3H), 6.850–7.30 (m, 8H)

1-[(RS,SR)-4-cyclohexyl-4-hydroxy-3-(2-fluorophenyl)-butyl]-4-[2-(2,2,2-trifluoroethoxy)-phenyl]-piperazine (Diastereoisomer with Upper TLC Rf) and 1-[(RR,SS)-4-cyclohexyl-4-hydroxy-3-(2-fluorophenyl)-butyl]-4-[2-(2,2,2-trifluoroethoxy)-phenyl]-piperazine (Diastereoisomer with Lower TLC Rf)

The title compounds were synthesised using the procedure described for the compound of Examples 1 and 2 but using the compound 3a as a starting material instead of the compound 1d. Purification by flash chromatography (petroleum ether-EtOAc-2 N ammonia in methanol 60:40:2) afforded the compound of the Example 3 as the diastereoisomer having the upper Rf (79%); the fractions containing the compound of Example 4 as the diastereoisomer having lower Rf were repurified by flash chromatography (petroleum ether-EtOAc-2 N ammonia in methanol 75:25:1) to give the pure product (3.5%).

Ex. 3: $^1$H-NMR (CDCl$_3$, δ): 0.80–1.40 (m, 6H), 1.45–1.80 (m, 4H), 1.85–2.10 (m, 3H), 2.21–2.45 (m, 2H), 2.50–2.75 (m, 4H), 2.95–3.26 (m, 4H), 3.30–3.42 (m, 1H), 3.50–3.60 (m, 1H), 3.70–4.30 (br, 1H, OH), 4.38 (q, 2H), 6.85–7.30 (m, 7H), 7.65–7.75 (m, 1H)

Ex. 4: $^1$H-NMR (CDCl$_3$, δ): 0.75–1.95 (m, 12H), 2.05–2.90 (m, 7H and OH), 3.00–3.30 (m, 5H), 3.65 (d, 1H), 4.38 (q, 2H), 6.85–7.40 (m, 8H)

EXAMPLE 5 (COMPARATIVE)

1-[(RS,SR)-4-Cyclohexyl-4-hydroxy-3-phenyl-butyl]-4-(2-methoxyphenyl)-piperazine Benzyl Cyclohexyl Ketone (Compound 5a)

To a solution of 11 ml of 0.5 M solution of benzyl zinc bromide in anhydrous tetrahydrofuran were added at 0° C. 5 mg of bis-triphenylphospinepalladium dichloride and 0.66 ml of cyclohexanecarbonyl chloride. The mixture was stirred at r.t. for 1.5 h, quenched with a saturated solution of ammonium chloride and extracted with ethyl acetate. The collected organic layers were washed with water, dried (Na$_2$SO$_4$) and the solvent was evaporated under vacuum. The crude was purified by flash chromatography eluting with petroleum ether-EtOAc 95:5 to give 0.78 g (52%) of the title compound.

$^1$H-NMR (200 MHz, CDCl$_3$, δ): 1.09–1.92 (m, 10H), 2.32–2.53 (m, 1H), 3.72 (s, 2H), 7.12–7.39 (m, 5H)

4-Cyclohexyl-4-oxo-3-phenyl-butyraldehyde Diethyl Acetal (Compound 5b)

To a solution of 1.78 g of Compound 5a in 30 ml of anhydrous dimethylformamide were added at r.t. 0.37 g of 60% sodium hydride oil dispersion and the mixture was stirred at r.t. for 1 h. 1.46 ml of 2-bromoacetaldeide diethyl acetal was added and the mixture stirred at r.t. for 1 h and at 80° C. for 1 h, cooled to r.t., quenched with water and extracted with EtOAc. The collected organic layers were washed with water, dried (Na$_2$SO$_4$) and the solvent was evaporated under vacuum. The crude was purified by flash chromatography eluting with petroleum ether-EtOAc 95:5 to give 1.17 g (42%) of the title compound.

$^1$H-NMR (200 MHz, CDCl$_3$, δ): 1.01–1.98 (m, 17H), 2.28–2.48 (m, 2H), 3.30–3.71 (m, 4H), 3.98 (t, 1H), 4.25 (t, 1H), 7.12–7.39 (m, 5H)

4-Cyclohexyl-4-oxo-3-phenyl-butyraldehyde (Compound 5c)

A solution of 1.17 g of Compound 5b in 10 ml of acetone and 22.1 ml of 2N HCl was stirred at r.t. for 5 h. After overnight resting, the aqueous layer was extracted with EtOAc. The collected organic layers were washed with water, dried (Na$_2$SO$_4$) and the solvent was evaporated under vacuum to give 0.84 g (100%) of the title compound used immediately without further purification.

1-(4-Cyclohexyl-4-oxo-3-phenyl-butyl)-4-(2-methoxyphenyl)-piperazine (Compound 5d)

To a solution of 0.84 g of Compound 5c and 1.19 g of 1-(2-methoxyphenyl)-piperazine in 30 ml of dichloromethane, 1.48 g of sodium triacetoxyborohydride and 0.98 ml of acetic acid were added and the resulting mixture was stirred at r.t. for 5 h. After overnight resting, the organic layer was washed with excess of 1M NaOH then with water, dried (Na$_2$SO$_4$) and the solvent was evaporated under vacuum. The crude was purified by flash chromatography eluting with petroleum ether-EtOAc 7:3 to give 1.45 g (99%) of the title compound.

$^1$H-NMR (200 MHz, CDCl$_3$, δ): 1.01–2.05 (m, 11H), 2.20–3.30 (m, 12H), 3.82 (s, 3H), 3.91–4.02 (m, 1H), 6.75–7.08 (m, 4H), 7.12–7.39 (m, 5H)

1-[(RS,SR)-4-Cyclohexyl-4-hydroxy-3-phenyl-butyl]-4-(2-methoxyphenyl)-piperazine Into a solution of 1.21 g of Compound 5d in 60 ml of dichloromethane at −78° C., was dropped 11.5 ml of 1 M solution of diisobutylaluminum hydride (DIBAL-H) in toluene. The mixture was stirred at −78° C. for 1 h, quenched at 40° C. with a saturated aqueous solution of NH$_4$Cl and extracted with chloroform. The collected organic layers were washed with water, dried (Na$_2$SO$_4$) and the solvent was evaporated under vacuum. The crude was purified by flash chromatography eluting with petroleum ether-EtOAc-2 N ammonia in methanol 30:70:2 to give 1.06 g (80%) of the title compound.

$^1$H-NMR (200 MHz, CDCl$_3$, δ): 1.01–1.38 (m, 6H), 1.51–1.78 (m, 4H), 1.86–2.02 (m, 3H), 2.22–2.38 (m, 3H), 2.52–2.78 (m, 4H), 2.75–2.95 (m, 1H), 3.02–3.20 (m, 4H), 3.48 (t, 1H), 3.82 (s, 3H), 6.80–7.03 (m, 4H), 7.10–7.38 (m, 5H).

EXAMPLE 6

Radioligand Binding to Different Receptors

6A. Human Recombinant 5-HT$_{1A}$ Receptors

Method:

A genomic clone coding for the human 5HT$_{1A}$-serotonergic receptor was stably transfected in a human cell line (HeLa). HeLa cells were grown as monolayers in Dulbecco's modified Eagle medium (DMEM), containing 10% fetal bovine serum, gentamycin (0.1 mg/ml) and 5% carbon dioxide, at 37° C. The cells were detached from the growth flask at 95% confluence by a cell scraper and were lysed in cold 5 mM Tris and 5 mM EDTA buffer (pH 7.4). The homogenates were centrifuged at 40000×g×20 minutes and the pellets were resuspended in a small volume of cold 5 mM Tris and 5 mM EDTA buffer (pH 7.4) and immediately frozen and stored at −70° C. until use.

[$^3$H]8-OH-DPAT binding: on the day of experiment, the cell membranes were resuspended in incubation buffer: 50 mM Tris HCl (pH 7.4), 2.5 mM MgCl$_2$, 10 mM pargyline (Fargin et al., Nature 335, 358–360, 1988). The membranes were incubated in a final volume of 1 ml for 30 minutes at 30° C. with 1 nM [$^3$H]8-OH-DPAT, in the absence or presence of the test compounds. Non-specific binding was determined in the presence of 10 μM 5-HT. Incubation was stopped by addition of cold Tris-HCl buffer and rapid filtration through a 0.2%-polyethyleneimine-pretreated Whatman-GF/B or Schleicher-&-Schuell-GF52 filter.

The affinity of the tested compounds was evaluated as inhibition of specific binding of the radioligand to 5-HT$_{1A}$ receptors (IC$_{50}$) by using the non-linear curve-fitting program (De Lean et al., Am. J. Physiol. 235, E97-E102, 1978). The IC$_{50}$ value was converted to an affinity constant (Ki) by the equation of Cheng et al., Biochem. Pharmacol. 22, 3099–3108 (1973).

[$^{35}$S]GTPγS binding: on the experimental day, cell membranes from HeLa cells transfected with human cloned 5-HT$_{1A}$ receptors were resuspended in buffer pH 7.4 containing 20 mM HEPES, 3 mM MgCl$_2$ and 120 mM NaCl (Stanton, J. A.; Beer, M. S. Eur. J. Pharmacol. 320, 267–275, 1997). The membranes were incubated with 10 μM GDP and decreasing concentrations of test drugs (from 100 μM to 0.1 nM) or decreasing concentrations of 5-HT (from 100 μM to 0.1 nM, reference curve) for 20 min at 30° C. in a final volume of about 0.25 ml. [$^{35}$S]GTPγS (200–250 μM in 10 μl) was added to samples and incubated for a further 30 min at 30° C. Non-specific binding was determined in the presence of 10 μM GTPγS. The incubation was stopped by addition of ice-cold HEPES buffer and rapid filtration on Unifilter GF/C filters, using a Filtermate cell harvester (Packard). The filters were washed four times with total 1.2 ml of same buffer. Radioactivity was counted by liquid scintillation spectrometry with efficiency >90% (TopCount Packard). Stimulation of [$^{35}$S]GTPγS binding induced by the compounds tested was espressed as % increase in binding above basal value, being the maximal stimulation observed with 5-HT taken as 100%. The concentration-response curve of the agonistic activity was analyzed by non linear fitting program (De Lean et al., Am. J. Physiol. 235, E97-E102, 1978).

A stimulation of [$^{35}$S]GTPγS binding represented the functional correlate of the binding of an agonist compound at the 5-HT$_{1A}$ receptors. Stimulation induced by the endogenous ligand 5-HT was considered the maximal stimulation attainable. Compounds stimulating [$^{35}$S]GTPγS binding at a lower level were considered as partial agonists. Compounds that do not stimulate [$^{35}$S]GTPγS binding were considered as neutral antagonists.

Results

The results reported in Table 1 show that the compounds of the invention tested have a high affinity for the 5-HT$_{1A}$ receptor. Compounds of Ex. 1, Ex. 1Y, Ex. 2 and Ex. 2X were more potent than Ex. 5 (statistical signficance p<0.01). With regard to the [$^{35}$S]GTPγS binding, compounds of Ex. 1X and 2Y were partial agonists inducing stimulation of the [$^{35}$S]GTPγS binding. The other compounds did not stimulate the [$^{35}$S]GTPγS binding, behaving as neutral antagonists.

TABLE 1

Binding at 5-HT$_{1A}$ receptors

| Compound | Affinity: Ki (nM) | Functional effect ([$^{35}$S]GTPγS binding) |
|---|---|---|
| Ex. 1 | 0.13 | Neutral antagonist |
| Ex. 1X | 0.50 | Partial agonist |
| Ex. 1Y | 0.37 | Neutral antagonist |
| Ex. 2 | 0.29 | Neutral antagonist |
| Ex. 2X | 0.24 | Neutral antagonist |
| Ex. 2Y | 0.98 | Partial agonist |
| Ex. 3 | 0.29 | Neutral antagonist |
| Ex. 4 | 0.68 | Neutral antagonist |
| Ex. 5 | 0.65 | Neutral antagonist |

6B. Human Recombinant α$_1$-Adrenoceptor Subtypes

Method:

Binding to cloned human α$_1$-adrenoceptor subtypes was performed in membranes from CHO cells (chinese hamster ovary cells) transfected by electroporation with DNA expressing the gene encoding each α$_1$-adrenoceptor subtype. Cloning and stable expression of the human α$_1$-adrenoceptor gene was performed as previously described (Testa et al. Pharmacol. Comm., 6: 79–86,1995).

CHO cells were grown in suspension in Iscove's modified Dulbecco's medium, supplemented with 10% fetal calf serum and gentamicin (50 µg/ml), at 37° C. in 7% CO$_2$ in an humidified incubator. Cells were collected by centrifugation, lised in ice-cold Tris 5 mM and EDTA 5 mM buffer (pH 7.4) and gently homogenised. Homogenates were centrifuged at 40000×g×20 min and pellets were resuspended in a small volume of ice-cold Tris 5 mM and EDTA 5 mM buffer (pH 7.4) and immediately frozen and stored at −80° C. until use.

CHO cell membranes were resuspended and incubated in 50 mM Tris, pH 7.4, with 0.2 nM [$^3$H]prazosin, in a final volume of 1.02 ml for 30 min at 25° C., in absence or presence of competing drugs. Non-specific binding was determined in the presence of 10 µM phentolamine. The incubation was stopped by rapid filtration through 0.2% polyethyleneimine pretreated Schleicher & Schuell GF52 filters using a Tomtec (PerkinElmer) cell harvester. The filters were washed with 3×1 ml of ice-cold Tris buffer, dried and the radioactivity was measured in a Betaplate (Wallac) liquid scintillation counter.

The inhibition of specific binding by the compounds was analysed to estimate the IC$_{50}$ value by the non-linear curve-fitting program Allfit (De Lean et al. Am. J. Physiol. 235, E97-E102, 1978). The IC$_{50}$ value is converted to an affinity constant (Ki) by the equation of Cheng & Prusoff (Biochem. Pharmacol. 22: 3099–3108, 1973).

Results

The results reported in Table 2 show that the compounds of the invention tested have different affinity for the α-adrenoceptor subtypes, being particularly potent at the α$_{1d}$-subtype. Selectivity (evaluated as ratio between Ki values at α$_1$-adrenoceptor subtypes and Ki value at 5-HT$_{1A}$ receptor) of the compounds of the invention was generally better than that of the compound described in the prior art (Ex. 5).

TABLE 2

Binding affinity (Ki, nM) for α$_1$-adrenoceptor subtypes and selectivity vs 5-HT$_{1A}$ receptors

| Compound | α$_{1a}$ | α$_{1b}$ | α$_{1d}$ | α$_{1a}$/5-HT$_{1A}$ | α$_{1b}$/5-HT$_{1A}$ | α$_{1d}$/5-HT$_{1A}$ |
|---|---|---|---|---|---|---|
| Ex. 1 | 18 | 5.9 | 1.0 | 138 | 45 | 7.7 |
| Ex. 1Y | 24 | 11 | 1.2 | 65 | 30 | 3.2 |
| Ex. 2X | 44 | 11 | 0.5 | 183 | 46 | 2.1 |
| Ex. 5 | 51 | 12 | 0.5 | 78 | 18 | 0.8 |

6C. Rat Recombinant D$_3$ Dopamine Receptors

Method:

Cloned rat D$_3$ dopamine receptors permanently expressed in CHO cells were used (Chio et al. Mol. Pharmacol. 45, 51–60, 1994). Membranes were prepared by mechanical disruption of cell pellets in ice cold 50 mM Tris, 5 mM EDTA, 5 mM EGTA, pH 7.4 followed by low (100 g), medium (20000 g) and high (80000 g) speed centrifugation steps. Competition radioligand binding experiments employed 11 drug concentrations run in duplicate in a scintillation proximity assay (SPA) format. The radioligand used was [$^3$H]-7-OH-DPAT (154 Ci/mmol). Nonspecific binding (75–95% of total) was defined with cold haloperidol added in excess (3 µM). Total binding was determined with buffer: 20 mM HEPES, 10 mM MgSO$_4$, 150 mM NaCl, 1 mM EDTA (pH 7.4). Binding mixtures were made in flexible, 96-well, Wallac Micro-Beta plates by the addition of 11 µl of drug dilution, 11 µl of radioligand, and 178 µl of membrane/SPA bead suspension (100 mg of WGA-coated SPA beads incubated with 5–15 µg protein/plate in 10 ml binding buffer for 30 minutes at room temperature followed by low-speed centrifugation and resuspension in 2 ml binding buffer). After sealing and incubation at room temperature for 1 hour the plates were counted in a Wallac Micro-Beta scintillation counter.

IC$_{50}$ values from both assay methods were estimated by fitting the data to a one-site competition model: $Y=T/(1+10^{log(X)-log(IC50)})$, where Y is the specific CPM's bound at concentration X and T is the specific CPM's bound in the absence of competitor. Inhibition constants (Ki) were calculated using the Cheng-Prushoff equation (Biochem. Pharmacol. 22: 3099–3108, 1973).

Results

The results reported in Table 3 show that the compounds of the invention tested have affinity for the D$_3$ subtype of dopaminergic receptor. Selectivity (evaluated as ratio between Ki values at D$_3$-dopaminergic subtype and Ki value at 5-HT$_{1A}$ receptor) of the compounds of the invention was better than that of the compound described in the prior art (Ex. 5).

TABLE 3

Binding affinity for D$_3$ dopamine receptors and selectivity vs 5-HT$_{1A}$ receptors

| Compound | Ki (nM) | D$_3$/5-HT$_{1A}$ |
|---|---|---|
| Ex. 1 | 12.5 | 96 |
| Ex. 1Y | 20 | 54 |

TABLE 3-continued

Binding affinity for $D_3$ dopamine receptors and selectivity vs 5-$HT_{1A}$ receptors

| Compound | Ki (nM) | $D_3$/5-$HT_{1A}$ |
| --- | --- | --- |
| Ex. 2X | 3 | 12 |
| Ex. 5 | 7 | 11 |

EXAMPLE 7

Effects on Rhythmic Bladder-Voiding Contractions Induced by Bladder Filling in Anaesthetised Rats A. Method:

Female Sprague-Dawley rats weighing 225–275 g (Crl: CD® (SD) IGS BR, Charles River Italia) were used. The animals were housed with free access to food and water and maintained on a forced 12-hour alternating light-dark cycle at 22–24° C. for at least one week, except during the experiment. The activity on rhythmic bladder voiding contractions was evaluated according to the method of Dray (Dray J., *Pharmacol. Methods,* 13:157, 1985), with some modifications as in Guarneri (Guarneri, *Pharmacol. Res.* 27:173, 1993). Briefly, the rats were anaesthetised by subcutaneous injection of 1.25 g/kg (5 ml/kg) urethane, after which the urinary bladder was catheterised via the urethra using PE 50 polyethylene tubing filled with physiological saline. The catheter was tied in place with a ligature around the external urethral orifice and was connected to conventional pressure transducers (Statham P23 ID/P23 XL). The intravesical pressure was displayed continuously on a chart recorder (Battaglia Rangoni KV 135 with DCI/TI amplifier). The bladder was then filled via the recording catheter by incremental volumes of warm (37° C.) saline until reflex bladder-voiding contractions occurred (usually 0.81.5 ml). For intravenous injection of bioactive compounds, PE 50 polyethylene tubing filled with physiological saline was inserted into the jugular vein.

From the cystometrogram, the number of contractions recorded 15 minutes before (basal values) and after treatment, as well as the mean amplitude of these contractions (mean height of the peaks in mmHg), was evaluated.

Since most compounds produced an effect that was relatively rapid in onset and led to a complete cessation of bladder contractions, bioactivity was conveniently estimated by measuring the duration of bladder quiescence (i.e., the length of the time during which no contractions occurred). The number of tested animals showing a reduction in the number of contractions higher than 30% of that observed in the basal period was recorded too.

To compare the potency of the tested compounds for inhibiting the bladder voiding contractions, equieffective doses which resulted in the disappearance of contractions for a time of 10 minutes ($ED_{10min}$) were computed by means of linear regression using the least square method. The extrapolated doses which induced a reduction in the number of contractions greater than 30% in 50% of the treated rats ($ED_{50}$) were evaluated by the method of Bliss (Bliss C. I., *Quart J. Pharm. Pharmacol.* 11, 192–216, 1938).

B. Results

The rapid distension of the urinary bladder in urethane-anaesthetised rats produced a series of rhythmic bladder-voiding contractions whose characteristics have been described (Maggi et al., *Brain Res.* 380:83, 1986; Maggi et al., *J. Pharmacol. Exp. Ther.,* 230: 500, 1984). The frequency of these contractions is related to the sensory afferent arm of reflex micturition and to the integrity of the micturition centre, while their amplitude depends on the function of the reflex efferent arm. In this model system, compounds that act mainly on the central nervous system (such as morphine) cause a block in voiding contractions, whereas drugs that act at the level of the detrusor muscle, such as oxybutynin, lower the amplitude of the bladder contractions.

The results obtained after administration of prior-art compounds and compounds of the invention are shown in Table 4.

The compounds of the invention were superior to the reference standards in blocking volume-induced rhythmic bladder contractions. Ex. 1Y was more potent than Ex. 5, being its extrapolated dose inducing 10 minutes of disappearance of the contractions at least 2 fold lower. Furthermore, after administration of 0.3 mg/kg of Ex. 1Y, bladder contractions disappeared for 24 min, whereas after administration of 0.3 mg/kg of Ex. 5 this time quoted 14 min only.

In comparison to compounds of the invention, oxybutynin had the effect of decreasing the amplitude of contractions in a dose-related manner, with an $ED_{50}$ value (the extrapolated dose inducing a 30% reduction of amplitude of the contractions in 50% of treated rats) of 240 µg/kg. At this dosage, oxybutynin did not cause a blockade of bladder contractions and this is due to its specific mechanism of action (antimuscarinic) that is different than that of the compounds of the invention.

TABLE 4

Effects on rhythmic bladder-voiding contractions after intravenous administration
Data represent the $ED_{10\ min}$ values (the extrapolated dose inducing 10 minutes of disappearance of the contractions), the $ED_{50}$ (frequency) values (the extrapolated doses inducing a reduction of the number of contractions > 30% in 50% of treated rats), and the $ED_{50}$ (amplitude) values (the extrapolated doses inducing a 30% reduction of amplitude of the contractions in 50% of treated rats).

| Compound | $ED_{10\ min}$ µg/kg | $ED_{50}$ (frequency) µg/kg | $ED_{50}$ (amplitude) µg/kg |
| --- | --- | --- | --- |
| Ex. 1 | 198 | 30 | n.a. |
| Ex. 1Y | 23 | 15 | n.a. |
| Ex. 5 | 66 | 18 | n.a. |
| Flavoxate | >10000 | 2648 | n.a. |
| Oxybutynin | 7770 | >10000 | 240 | n.a. = not active; no significant reduction of the height of the peaks

EXAMPLE 8

Effect on Cystometric Parameters in Conscious Rats After Oral Administration

A. Method:

Male Sprague-Dawley rats [Crl: CD® (SD) IGS BR] of 300–400 g supplied by Charles River Italia were used. The animals were housed with free access to food and water and maintained on a forced 12-hour-light/12-hour-dark cycle at 22–24° C. of temperature, except during the experiment. To quantify urodynamic parameters in conscious rats, cystometrographic studies were performed according to the procedure previously reported (Guarneri et al., Pharmacol. Res. 24: 175, 1991).

Briefly, the rats were anaesthetised by intraperitoneal administration of 3 ml/kg of Equithensin solution (pentobarbital 30 mg/kg and chloral hydrate 125 mg/kg) and placed in a supine position. An approximately 10 mm-long midline incision was made in the shaved and cleaned abdominal wall. The urinary bladder was gently freed from adhering tissues, emptied and then cannulated via an incision in the bladder body, using a polyethylene cannula (0.58-mm internal diameter, 0.96-mm external diameter) which was permanently sutured with silk thread. The cannula was exteriorised through a subcutaneous tunnel in the retroscapular area, where it was connected to a plastic adapter in order to avoid the risk of removal by the animal. For drug testing, the rats were utilised one day after implantation.

On the day of the experiment, the rats were placed in modified Bollman cages, i.e., restraining cages that were large enough to permit the rats to adopt a normal crouched posture, but narrow enough to prevent turning around. After a stabilisation period of about 20 minutes, the free tip of the bladder cannula was connected through a T-shaped tube to a pressure transducer (Statham P23XL) and to a peristaltic pump (Gilson minipuls 2) for continues infusion of a warm (37° C.) saline solution into the urinary bladder, at a constant rate of 0.1 ml/minute. The intraluminal-pressure signal during infusion of saline into the bladder was continuously recorded on a polygraph (Rectigraph-8K San-ei with BM614/2 amplifier from Biomedica Mangoni). The cystometrogram was used to evaluate the urodynamic parameters of bladder volume capacity (BVC) and micturition pressure (MP). BVC (ml) is defined as the volume of saline infused into the bladder necessary to induce detrusor contraction followed by micturition. MP (mmHg) is defined as the maximal intravesical pressure caused by contraction during micturition. Basal BVC and MP values were evaluated as mean of the values observed in the cystometrograms recorded in an initial period of 30–60 minutes. Following determination of basal BVC and MP, the infusion was interrupted and the test compounds were administered orally by a stomach tube. Bladder infusion was resulmed and changes in BVC and MP were evaluated from the mean values obtained in the cystometrograms observed during 1, 2, 3, 4 and 5 hours after treatment. Compounds were administered in a volume of 2 ml/kg and groups of control animals received the same amount of vehicle (0.5% methocel in water) orally.

Results are shown in the accompanying figures.

FIG. 1 shows a time course of BVC and MP changes in rats after oral administration of vehicle (circles) or 10.0 mg/kg of the compound 1-[4-cyclohexyl-4-hydroxy-3-(2-fluorophenyl)-butyl]-4-(2-methoxyphenyl)-piperazine; upper TLC Rf) of Example 1 (squares). Data represent the % changes versus basal values at different times from treatment. "n"=number of rats/group. Significance shown as P< . . . (between treatments: ANOVA of CONTRAST VARIABLES) indicates the difference between the trend observed in the control (vehicle) and treated groups. Asterisks (*=p<0.05, =p<0.01 and *=p<0.001) indicate significance between the value observed at the time reported and the baseline value (within treatment).

Figure 2:
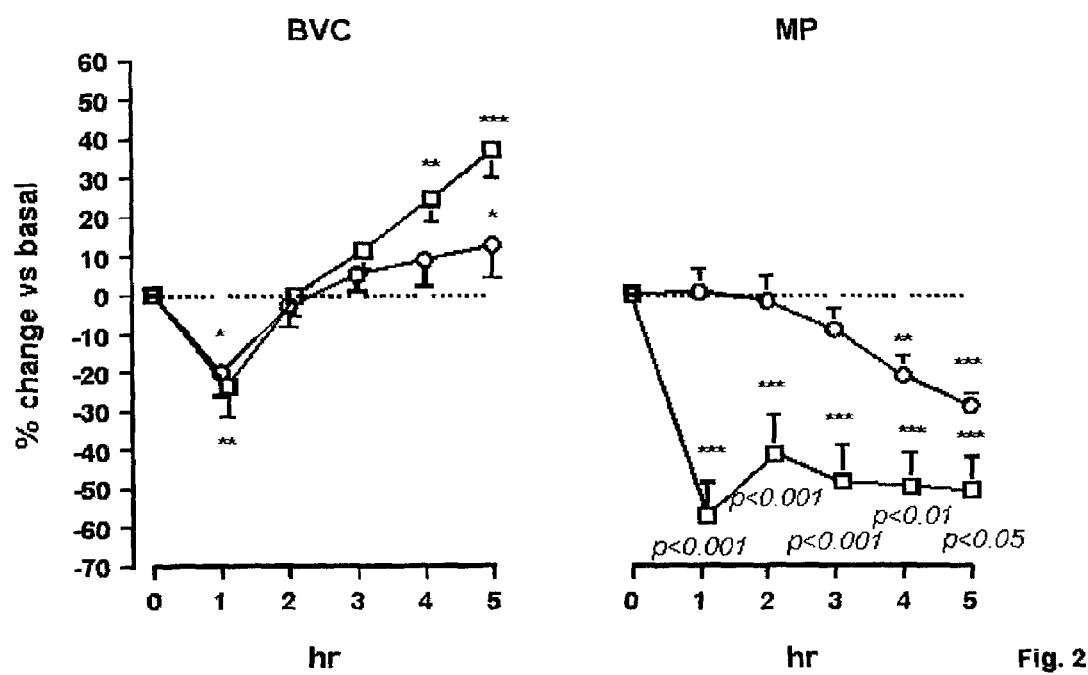
FIG. 2 shows the change versus time of bladder volume capacity (BVC) and micturition pressure (MP) in rats after oral administration of vehicle (circles) or 3.0 mg/kg of oxybutynin (squares).

FIG. 2 is a time-course of BVC and MP changes in rats after oral administration of vehicle (circles) or 3.0 mg/kg of oxybutynin (squares). Data are expressed as in FIG. 1.

Statistical Analysis

Data were expressed as mean±standard error. The percent changes of BVC and MP versus the basal values, as well as A values (difference in ml or mmHg) of BVC and MP (BVC or MP at time "x" minus basal value), are also evaluated for each rat/time. In the figures, data were reported as % changes versus basal values.

Statistical analysis on BVC and MP values, as well as on A values, was performed by S.A.S./STAT software, version 6.12. The observed differences between vehicle (control) and test treatments were evaluated on A values of BVC and MP, whereas the differences between the values at different times versus basal values were analyzed on original BVC and MP data.

EXAMPLE 9

Inhibition of Stereotypy (Rhythmic Forepaw Treading) Induced by 8-OH-DPAT in Rats (Post-Synaptic Antagonism)

A. Method:

The inhibitory effect of 5-$HT_{1A}$-receptor antagonists on stereotyped forepaw treading induced in rats by subcutaneous injection of 8-OH-DPAT was evaluated by the method of Tricklebank (Tricklebank et al., *Eur. J. Pharmacol.*, 117: 15, 1985) with minor modifications as described below.

Male Sprague-Dawley rats [Crl: CD® (SD) IGS BR] weighing 150–175 g from Charles River Italia were used. The animals were housed with free access to food and water and maintained on a forced 12-hour-light/12-hour-dark cycle at 22–24° C. of temperature. On the day of the experiment, the rats were placed singly in clear plastic containers, 10–15 minutes before administration of the vehicle or compounds to be tested. For evaluation of antagonistic activity after intravenous or oral administration, the compounds were administered 1 and 4 hours before induction of stereotypy by 8-OH-DPAT (1 mg/kg subcutaneously). Observation sessions lasted 30 seconds and began 3 minutes after 8-OH-DPAT treatment and were repeated every 3 minutes over a period of 15 minutes.

The appearance of the symptom induced by postsynaptic stimulation of 5-$HT_{1A}$ receptors was noted, and the intensity was scored using an intensity scale in which: 0=absent, 1=equivocal, 2=present and 3=intense. Behavioural scores for treated rats were accumulated throughout the observation time (5 observation periods) and expressed as mean values of 4 rats/dose. Change in mean values of treated animals in comparison with control (vehicle) group, expressed as percent inhibition, was used to quantify the antagonistic activity.

B. Results:

The results are shown in Table 5. These results demonstrate that administration of the compounds of invention lead to significant and long-lasting post-synaptic 5-$HT_{1A}$-receptor antagonist activity. In order to evaluate the potency of the compounds of invention for inhibiting the stereotypy (rhythmic forepaw treading) induced by 8-OH-DPAT an $ED_{75}$ value (equieffective dose inhibiting the forepaw treading by 75%) was evaluated by means of linear regression using the least square method.

After intravenous administration, the compounds of Ex. 2X, Ex. 1Y and Ex. 5 were practically equipotent. After oral administration, Ex. 1Y was more potent than Ex. 5, in particular at four hours after administration.

TABLE 5

Inhibition of forepaw treading induced by 8-OH-DPAT in rats
(post-synaptic antagonism)

| Compound | Dose (mg/kg) | % Inhibition of forepaw treading | |
|---|---|---|---|
| | | 1 h | 4 h |
| Ex. 1 | 10 p.o. | 100 | 96 |
| Ex. 1 | 3 p.o. | 84 | 72 |
| Ex. 1 | 1 p.o. | 35 | 37 |
| Ex. 1 | 1 h p.o.: $ED_{75}$ = 3.3 mg/kg/ | | |
| | 4 h p.o.: $ED_{75}$ = 4.0 mg/kg | | |
| Ex. 1Y | 0.3 i.v. | 100 | 84 |
| Ex. 1Y | 0.1 i.v. | 100 | 65 |
| Ex. 1Y | 0.03 i.v. | 72 | 35 |
| Ex. 1Y | 0.01 i.v. | 37 | 11 |
| Ex. 1Y | 1 h i.v.: $ED_{75}$ = 0.038 mg/kg/ | | |
| | 4 h i.v.: $ED_{75}$ = 0.182 mg/kg | | |
| Ex. 1Y | 3 p.o. | 92 | 85 |
| Ex. 1Y | 1 p.o. | 58 | 38 |
| Ex. 1Y | 0.3 p.o. | 18 | 18 |
| Ex. 1Y | 1 h p.o.: $ED_{75}$ = 1.7 mg/kg/ | | |
| | 4 h p.o.: $ED_{75}$ = 2.6 mg/kg | | |
| Ex. 2X | 0.3 i.v. | 100 | 89 |
| Ex. 2X | 0.1 i.v. | 100 | 63 |
| Ex. 2X | 0.03 i.v. | 65 | 49 |
| Ex. 2X | 0.01 i.v. | 39 | 6 |
| Ex. 2X | 1 h i.v.: $ED_{75}$ = 0.041 mg/kg/ | | |
| | 4 h i.v.: $ED_{75}$ = 0.152 mg/kg | | |
| Ex. 5 | 0.3 i.v. | 100 | 85 |
| Ex. 5 | 0.1 i.v. | 100 | 72 |
| Ex. 5 | 0.03 i.v. | 82 | 54 |
| Ex. 5 | 0.01 i.v. | 41 | 26 |
| Ex. 5 | 1 h i.v.: $ED_{75}$ = 0.032 mg/kg/ | | |
| | 4 h i.v.: $ED_{75}$ = 0.138 mg/kg | | |
| Ex. 5 | 3 | 90 | 67 |
| Ex. 5 | 1 | 42 | 46 |
| Ex. 5 | 0.3 | 8 | 20 |
| Ex. 5 | 1 h p.o.: $ED_{75}$ = 2.1 mg/kg/ | | |
| | 4 h p.o.: $ED_{75}$ = 4.6 mg/kg | | |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that values are approximate, and are provided for description.

Patents, patent applications, publications, procedures, and the like are cited throughout this application, the disclosures of which are incorporated herein by reference in their entireties.

The invention claimed is:

1. A compound having the general formula I

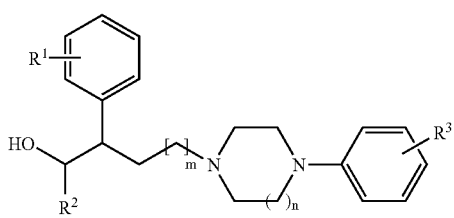

wherein:
$R^1$ represents a halogen atom,
$R^2$ represents a $(C_3-C_8)$-cycloalkyl group,
$R^3$ represents a $(C_1-C_4)$-haloalkoxy group,
m is 1 or 2, and
n is 1,
or an enantiomer, optical isomer, diastereomer, N-oxide, crystalline form, hydrate, or pharmaceutically acceptable salt thereof.

2. A compound which is 1-[4-cyclohexyl-4-hydroxy-3-(2-fluorophenyl)-butyl]-4-[2-(2,2,2-trifluoroethoxy)-phenyl]-piperazine or an N-oxide, crystalline form, hydrate, or pharmaceutically acceptable salt thereof, in the form of any of its isolated stereoisomers 1-[(3R,4S)-4-cyclohexyl-4-hydroxy-3-(2-fluorophenyl)-butyl]-4-[2-(2,2,2-trifluoroethoxy)-phenyl]-piperazine,
1-[(3S,4R)-4-cyclohexyl-4-hydroxy-3-(2-fluorophenyl)-butyl]-4-[2-(2,2,2-trifluoroethoxy)-phenyl]-piperazine,
1-[(3R,4R)-4-cyclohexyl-4-hydroxy-3-(2-fluorophenyl)-butyl]-4-[2-(2,2,2-trifluoroethoxy)-phenyl]-piperazine,
1-[(3S,4S)-4-cyclohexyl-4-hydroxy-3-(2-fluorophenyl)-butyl]-4-[2-(2,2,2-trifluoroethoxy)-phenyl]-piperazine,
or a mixture of any two or more of the foregoing in any proportion.

3. A method for treating disorders of the urinary tract in a mammal in need thereof, comprising administering an effective amount of a compound having the general formula I

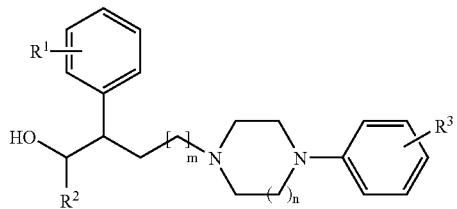

wherein:
$R^1$ represents a halogen atom,
$R^2$ represents a $(C_3-C_8)$-cycloalkyl group,
$R^3$ represents a $(C_1-C_4)$-haloalkoxy group,
m is 1 or 2, and
n is 1 or 2,
or an enantiomer, optical isomer, diastereomer, N-oxide, crystalline form, hydrate, or pharmaceutically acceptable salt thereof.

4. The method according to claim 3 wherein the administered compound is 1-[4-cyclohexyl-4-hydroxy-3-(2-fluorophenyl)-butyl]-4-[2-(2,2,2-trifluoroethoxy)-phenyl]-piperazine or an N-oxide, crystalline form, hydrate, or pharmaceutically acceptable salt thereof in the form of any of its isolated stereoisomers:

1-[(3R,4S)-4-cyclohexyl-4-hydroxy-3-(2-fluorophenyl)-butyl]-4-[2-(2,2,2-trifluoroethoxy)-phenyl]-piperazine,
1-[(3S,4R)-4-cyclohexyl-4-hydroxy-3-(2-fluorophenyl)-butyl]-4-[2-(2,2,2-trifluoroethoxy)-phenyl]-piperazine,
1-[(3R,4R)-4-cyclohexyl-4-hydroxy-3-(2-fluorophenyl)-butyl]-4-[2-(2,2,2-trifluoroethoxy)-phenyl]-piperazine,
1-[(3S,4S)-4-cyclohexyl-4-hydroxy-3-(2-fluorophenyl)-butyl]-4-[2-(2,2,2-trifluoroethoxy)-phenyl]-piperazine,
or a mixture of any two or more of the foregoing in any proportion.

* * * * *